(12) United States Patent
de Groot et al.

(10) Patent No.: US 7,468,799 B2
(45) Date of Patent: Dec. 23, 2008

(54) SCANNING INTERFEROMETRY FOR THIN FILM THICKNESS AND SURFACE MEASUREMENTS

(75) Inventors: Peter J. de Groot, Middletown, CT (US); Xavier Colonna de Lega, Middletown, CT (US)

(73) Assignee: Zygo Corporation, Middlefield, CT (US)

( * ) Notice: Subject to any disclaimer, the term of this patent is extended or adjusted under 35 U.S.C. 154(b) by 0 days.

(21) Appl. No.: 12/020,351

(22) Filed: Jan. 25, 2008

(65) Prior Publication Data

US 2008/0180694 A1 Jul. 31, 2008

Related U.S. Application Data

(63) Continuation of application No. 10/974,466, filed on Oct. 27, 2004, now Pat. No. 7,324,210.

(60) Provisional application No. 60/515,140, filed on Oct. 27, 2003.

(51) Int. Cl.
G01B 9/02 (2006.01)
G01B 11/28 (2006.01)
(52) U.S. Cl. ............... 356/504; 356/497; 356/630; 356/516
(58) Field of Classification Search ............. 356/479, 356/497, 456, 481, 517, 511, 512, 503, 504, 356/630, 632, 489, 495, 516
See application file for complete search history.

(56) References Cited

U.S. PATENT DOCUMENTS

| | | | |
|---|---|---|---|
| 4,355,903 A | 10/1982 | Sandercock | |
| 4,576,479 A | 3/1986 | Downs | |
| 4,618,262 A | 10/1986 | Maydan et al. | |
| 4,660,980 A | 4/1987 | Takabayashi et al. | |
| 4,818,110 A | 4/1989 | Davidson | |
| 4,999,014 A | 3/1991 | Gold et al. | |
| 5,042,949 A | 8/1991 | Greenberg et al. | |
| 5,042,951 A | 8/1991 | Gold et al. | |
| 5,112,129 A | 5/1992 | Davidson et al. | |
| 5,129,724 A | 7/1992 | Brophy et al. ............... 356/357 |

(Continued)

FOREIGN PATENT DOCUMENTS

DE 4108944 9/1992

(Continued)

OTHER PUBLICATIONS

U.S. Appl. No. 11/335,873, filed Jan. 19, 2006, Colonna de Lega et al.

(Continued)

*Primary Examiner*—Patrick J Connolly
(74) *Attorney, Agent, or Firm*—Fish & Richardson P.C.

(57) ABSTRACT

A method including: providing a low coherence scanning interferometry data for at least one spatial location of a sample having multiple interfaces, wherein the data is collected using a low coherence scanning interferometer having an illumination geometry and an illumination frequency spectrum, and wherein the data comprises a low coherence scanning interferometry signal having multiple regions of fringe contrast corresponding to the multiple interfaces; and determining a distance between at least one pair of interfaces based on a distance between the corresponding regions of fringe contrast and information about the illumination geometry.

21 Claims, 11 Drawing Sheets

U.S. PATENT DOCUMENTS

| | | | |
|---|---|---|---|
| 5,133,601 | A | 7/1992 | Cohen et al. |
| 5,135,307 | A | 8/1992 | de Groot et al. |
| 5,301,010 | A | 4/1994 | Jones et al. |
| 5,390,023 | A * | 2/1995 | Biegen ............. 356/497 |
| 5,398,113 | A | 3/1995 | de Groot et al. |
| 5,459,564 | A | 10/1995 | Chivers |
| 5,587,792 | A | 12/1996 | Nishizawa et al. |
| 5,589,938 | A | 12/1996 | Deck |
| 5,602,643 | A | 2/1997 | Barrett |
| 5,774,224 | A | 6/1998 | Kerstens |
| 5,900,633 | A | 5/1999 | Solomon et al. |
| 6,242,739 | B1 | 6/2001 | Cherkassky |
| 6,249,351 | B1 | 6/2001 | de Groot |
| H1972 | H | 7/2001 | Inoue |
| 6,259,521 | B1 | 7/2001 | Miller et al. |
| 6,377,349 | B1 | 4/2002 | Fercher |
| 6,500,591 | B1 | 12/2002 | Adams |
| 6,507,405 | B1 | 1/2003 | Grek et al. |
| 6,545,761 | B1 | 4/2003 | Aziz et al. |
| 6,545,763 | B1 | 4/2003 | Kim et al. |
| 6,597,460 | B2 | 7/2003 | Groot et al. |
| 6,624,894 | B2 | 9/2003 | Olszak et al. |
| 6,636,322 | B1 | 10/2003 | Terashita |
| 6,721,094 | B1 | 4/2004 | Sinclair et al. |
| 6,775,006 | B2 | 8/2004 | de Groot et al. |
| 6,934,035 | B2 | 8/2005 | Yang et al. |
| 6,940,604 | B2 | 9/2005 | Jung et al. |
| 7,106,454 | B2 | 9/2006 | de Groot et al. |
| 7,139,081 | B2 | 11/2006 | de Groot et al. |
| 7,271,918 | B2 | 9/2007 | de Groot et al. |
| 7,277,183 | B2 | 10/2007 | Deck |
| 7,283,248 | B2 | 10/2007 | Hill |
| 7,289,224 | B2 | 10/2007 | de Lega et al. |
| 7,289,225 | B2 | 10/2007 | de Groot |
| 7,292,346 | B2 | 11/2007 | de Groot et al. |
| 7,298,494 | B2 | 11/2007 | de Groot |
| 2006/0012582 | A1 | 1/2006 | de Lega |
| 2006/0158657 | A1 | 7/2006 | Colonna de Lega et al. |
| 2006/0158658 | A1 | 7/2006 | Colonna de Lega et al. |
| 2006/0158659 | A1 | 7/2006 | Colonna de Lega et al. |
| 2006/0176522 | A1 * | 8/2006 | Mansfield et al. ........... 358/474 |
| 2007/0081167 | A1 | 4/2007 | de Groot |
| 2007/0097380 | A1 | 5/2007 | de Groot et al. |
| 2008/0049222 | A1 * | 2/2008 | Yamaguchi et al. ......... 356/328 |

FOREIGN PATENT DOCUMENTS

| | | |
|---|---|---|
| DE | 4309056 | 9/1994 |
| EP | 0 397 388 A2 | 11/1990 |
| EP | 0 549 166 A2 | 6/1993 |
| EP | 0 617 255 A1 | 9/1994 |
| EP | 0 929 094 A2 | 7/1999 |
| GB | 2385417 | 8/2003 |
| WO | WO 97/44633 | 11/1997 |
| WO | WO 02/082008 | 10/2002 |
| WO | WO 03/062802 | 7/2003 |
| WO | WO 2004/023071 | 3/2004 |

OTHER PUBLICATIONS

U.S. Appl. No. 11/335,871, filed Jan. 19, 2006, Colonna de Lega et al.
U.S. Appl. No. 11/334,949, filed Jan. 19, 2006, Colonna de Lega et al.
C. Akcay et al., "Spectral shaping to improve the point spread function in optical coherence tomography", *Optics Letters*, vol. 28 No. 20, pp. 1921-1923 (Oct. 15, 2003).
R.M.A. Azzam et al., "Reflection and Transmission of Polarized Light by Stratified Planar Structures", *Ellipsometry and Polarized Light*, Elsevier Science B.V. ISBN 0 444 87016 4 (Paperback) pp. 267-363 (1987).
M. Bashkansky et al., "Signal Processing for Improving Field Cross-correlation Function in Optical Coherence Tomography", *Supplement to Optics & Photonics News*, 9(5) (May 1998).
A. Bosseboeuf et al., "Application of microscopic interferometry techniques in the MEMS field", *Proceedings of SPIE*, vol. 5145, pp. 1-16 (2003).
M. Davidson et al., "An Application of Interference Microscopy to Integrated Circuit Inspection and metrology", *Proceedings SPIE*, vol. 775, pp. 233-247 (1987).
T. Dresel et al., "Three-dimensional sensing of rough surfaces by coherence radar", *Applied Optics*, vol. 31, No. 7, pp. 919-925 (Mar. 1, 1992).
J.E. Greivenkamp, "Generalized data reduction for heterodyne interferometry", *Optical Engineering.*, vol. 23 No. 4, pp. 350-352 (Jul./Aug. 1984).
P. de Groot, "Derivation of algorithms for phase-shifting interferometry using the concept of a data-sampling window", *Appl. Opt.*, 34(22), p. 4723-4730 (1995).
P. de Groot et al., "Signal modeling for modern interference microscopes", *SPIE Proceedings*, 5457-4 (2004).
Peter de Groot et al., "Determination of fringe order in white-light interference microscopy", *Appl. Opt.*, 41(22) pp. 4571-4578 (2002).
Feke, Gilbert D. et al., "Interferometric back focal plane microellipsometry", *Applied Optics*, vol. 37, No. 10, pp. 1796-1802 (Apr. 1, 1998).
P.A. Flournoy et al., "White-light interferometric thickness gauge", *Appl. Opt.*, 11(9), pp. 1907-1915 (1972).
G. Hausler et al., "Coherence Radar and Spectral Radar—New Tools for Dermatological Diagnosis", *Journal of Biomedical Optics*, vol. 3, No. 1, pp. 21-31 (Jan. 1998).
R.D. Holmes et al., "Scanning microellipsometry for extraction of true topograpy", *Electronics Letters*, vol. 31, No. 5, pp. 358-359 (Mar. 2, 1995).
Kim, Seung-Woo et al., "Thickness-profile measurement of transparent thin-film layers by white-light scanning interferometry", *Applied Optics*, vol. 38, No. 28, pp. 5968-5973 (Oct. 1, 1999).
Kino, Gordon S. et al., "Mirau correlation microscope", *Applied Optics*, vol. 29, No. 26, pp. 3775-3783 (Sep. 10, 1990).
Kieran G. Larkin, "Efficient nonlinear algorithm for envelope detection in white light interferometry", *Journal of the Optical Society of America A*, vol. 13, No. 4, pp. 832-843 (1996).
Kujawinska, Malgorzata, "Spatial Phase Measurement Methods", *Interferogram Analysis: Digital Fringe Pattern Measurement Techniques*, IOP Publishing Ltd. 1993, pp. 141-193.
Lee et al., "Profilometry with a coherence scanning microscope", *Appl. Opt.*, 29(26), pp. 3784-3788 (1990).
I. Lee-Bennett, "Advances in non-contacting surface metrology", *OF&T Workshop*, papter OTuC1 (2004).
K. Leonhardt et al., "Micro-Ellipso-Height-Profilometry", *Optics Communications*, vol. 80, No. 3, 4, pp. 205-209 (Jan. 1, 1991).
Y. Liu et al., "Common path interferometric microellipsometry", *SPIE*, vol. 2782, pp. 635-645 (1996).
C.J. Morgan, "Least-Squares estimation in phase-measurement interferometry", *Optics Letters*, 7(8), pp. 368-370 (1982).
Ngoi et al., "Phase-shifting interferometry immune to vibration", *Applied Optics*, vol. 40, No. 19, pp. 3211-3214 (2001).
A.V. Oppenheim et al., "10.3: The time-dependent Fourier Transform", *Discrete-Time Signal Processing*, 2nd Edition, pp. 714-722 (Prentice Hall, New Jersey, 1999).
M.C. Park et al., "Direct quadratic polynomial fitting for fringe peak detection of white light scanning interferograms", *Optical Engineering*, vol. 39, No. 4, pp. 952-959 (2000).
S. Pettigrand et al., "Mesures 3D de topographies et de vibrations a l'echelle (sub)micrometrique par microscopie optique interferometrique", *Proc. Club CMOI, Methodes et Techniques Optiques pour l'Industrie*, (2002).
M. Pluta, "Advanced light microscopy", vol. 3, PWN—Polish Scientific Publishers (Elsevier, Amsterdam), pp. 265-271 (1993).
W.H. Press et al., "Linear Correlation", *Numerical Recipes in C*, Cambridge University Press, 2nd Edition, pp. 636-639 (1992).
Rosencwaig, Allan et al., "Beam profile reflectometry: A new technique for dielectric film measurements", *Applied Physics Letters*, vol. 60, No. 11, pp. 1301-1303 (Mar. 16, 1992).
P. Sandoz et al., "Optical implementation of frequency domain analysis for white light interferometry", *Proceedings SPIE*, vol. 2545, pp. 221-228 (Jun. 1995).

P. Sandoz et al., "High-resolution profilometry by using phase calculation algorithms for spectroscopic analysis of white-light interferograms", *Journal of Modern Optics*, vol. 43, No. 4, pp. 701-708 (1996).

Sandoz, Patrick "Wavelet transform as a processing tool in white-light interferometry", *Optics Letters*, vol. 22, No. 14, pp. 1065-1067 (Jul. 15, 1997).

P. Sandoz et al., "Processing of white light correlograms: simultaneous phase and envelope measurements by wavelet transformation", *SPIE*, vol. 3098, pp. 73-82 (1997).

U. Schnell et al., "Dispersive white-light interferometry for absolute distance measurement with dielectric multilayer systems on the target", *Optics Letters*, vol. 21, No. 7, pp. 528-530 (Apr. 1996).

J. Schwider et al., "Dispersive interferometric profilometer", *Optics Letters*, vol. 19, No. 13, pp. 995-997 (Jul. 1994).

C.W. See et al., "Scanning optical microellipsometer for pure surface profiling", *Applied Optics*, vol. 35, No. 34, pp. 6663-6668 (Dec. 1, 1996).

Shatalin, S.V. et al., "Reflection conoscopy and micro-ellipsometry of isotropic thin film structures", *Journal of Microscopy*, vol. 179, Part 3, pp. 241-252 (Sep. 1995).

M. Totzeck, "Numerical simulation of high-NA quantitative polarization microscopy and corresponding near-fields", *Optik*, vol. 112, No. 9, pp. 399-406 (2001).

R. Tripathi et al., "Spectral shaping for non-Gaussian source spectra in optical coherence tomography", *Optics Letters*, vol. 27, No. 6, pp. 406-408 (Mar. 15, 2002).

D. Willenborg et al, "A novel micro-spot dielectric film thickness measurement system", *SPIE*, vol. 1594, pp. 322-333 (1991).

C. J. R. Sheppard et al. "Effect of numerical aperture on interference fringe spacing". Applied Optics 34(22):4731-4734, Aug. 1995.

I Abdulhalim. "Spectroscopic interference microscopy technique for measurement of layer parameters". Measurement Science and Technology 12:1996-2001, 2001.

P. de Groot et al. "Angle-resolved three-dimensional analysis of surface films by coherence scanning interferometry", Optics Letters 32(12): 1638-1640, Jun. 2007.

de Groot, et al., "Signal modeling for low-coherence height-scanning interference microscopy", *Applied Optics*, vol. 43, No. 25 (Sep. 1, 2004).

Lyakin et al., "The interferometric system with resolution better than coherence length for determination of geometrical thickness and refractive index of a layer object", *Proceedings of the SPIE—The International Society for Optical Engineering SPIE-INT. Soc. Opt. Eng USA*, vol. 4956, pp. 163-169 (Jul. 2003).

A Communication from a foreign patent office dated Mar. 9, 2005.

R.M.A. Azzam et al, "Ellipsometric function of a film-substrate system: Applications to the design of reflection-type optical devices and to ellipsometry", *Journal of the Optical Society of America*, vol. 5, No. 3, pp. 252-260 (Mar. 1975).

Berman et al., "Review of In Situ & In-line Detection for CMP Applications", *Semiconductor Fabtech - 8th Edition*, pp. 267-274 (1998).

\* cited by examiner

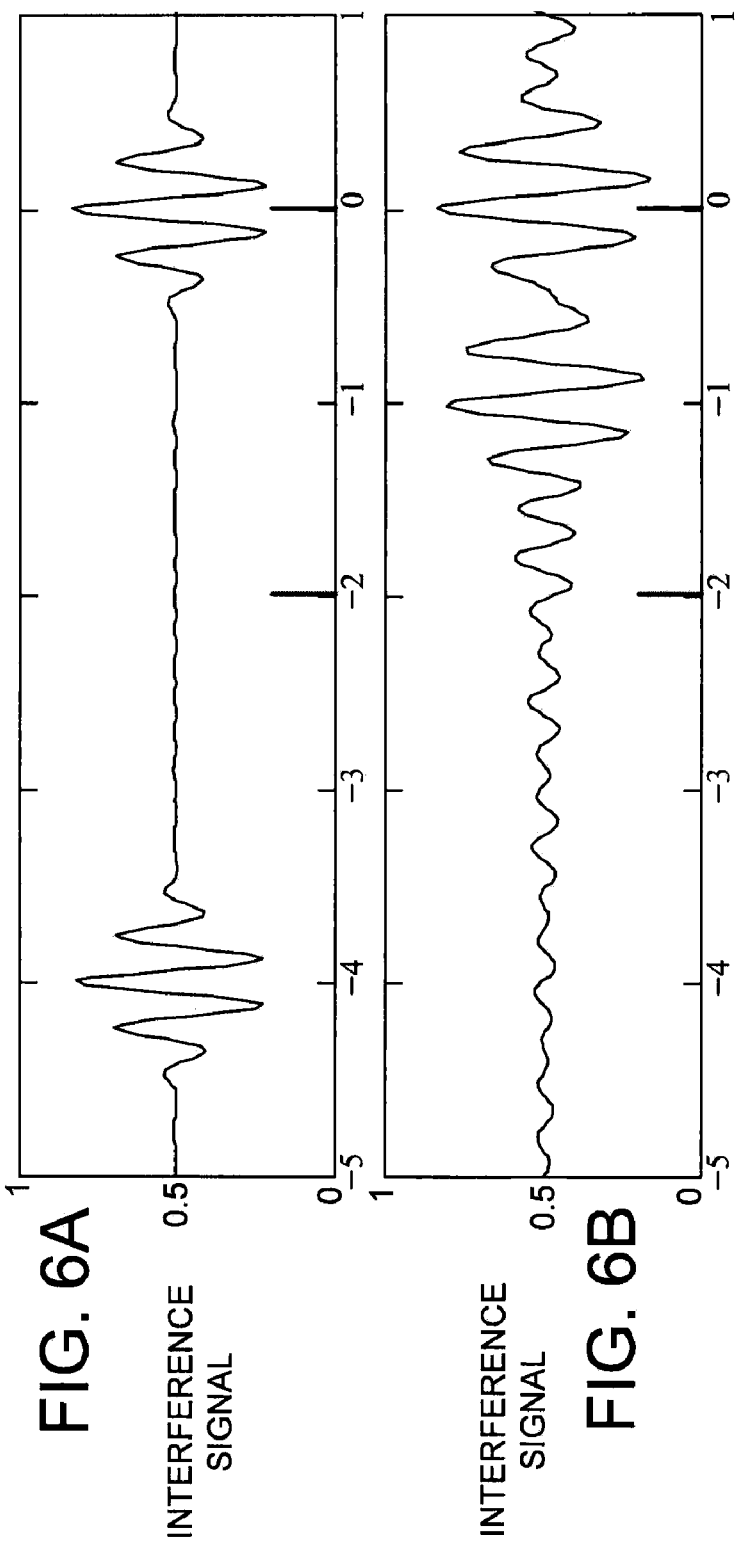

SCANNING INTERFEROMETRY FOR THIN FILM THICKNESS AND SURFACE MEASUREMENTS

CROSS-REFERENCE TO RELATED APPLICATIONS

This application is a continuation of U.S. application Ser. No. 10/974,466, entitled "SCANNING INTERFEROMETRY FOR THIN FILM THICKNESS AND SURFACE MEASUREMENTS," filed on Oct. 27, 2004, now U.S. Pat. No. 7,324,210, which claims priority under 35 U.S.C. 119(e) to U.S. Provisional Patent Application: U.S. Patent Application Ser. No. 60/515,140 filed Oct. 27, 2003 and entitled "THIN FILM THICKNESS AND SIMULTANEOUS SURFACE TOPOGRAPHY MEASUREMENT USING SCANNING INTERFEROMETRY," by Peter J. de Groot et al., the contents both of which are incorporated herein by reference.

BACKGROUND

The invention relates to using scanning interferometry to measure thickness(es), surface topography, and/or other characteristics of objects having complex surface structures, such as thin film(s).

Interferometric techniques are commonly used to measure the profile of a surface of an object. To do so, an interferometer combines a measurement wavefront reflected from the surface of interest with a reference wavefront reflected from a reference surface to produce an interferogram. Fringes in the interferogram are indicative of spatial variations between the surface of interest and the reference surface.

A scanning interferometer scans the optical path length difference (OPD) between the reference and measurement legs of the interferometer over a range comparable to, or larger than, the coherence length of the interfering wavefronts, to produce a scanning interferometry signal for each camera pixel used to measure the interferogram. A limited coherence length can be produced, for example, by using a white-light source, which is referred to as scanning white light interferometry (SWLI). A typical scanning white light interferometry (SWLI) signal is a few fringes localized near the zero optical path difference (OPD) position. The signal is typically characterized by a sinusoidal carrier modulation (the "fringes") with bell-shaped fringe-contrast envelope. The conventional idea underlying SWLI metrology is to make use of the localization of the fringes to measure surface profiles. Scanning interferometers that use a limited coherence length to localize interference fringes in the interferometry signal are also referred to as "low coherence scanning interferometers."

Typically, there are two approaches to processing such data. The first approach is to locate the peak or center of the envelope, assuming that this position corresponds to the zero optical path difference (OPD) of a two-beam interferometer for which one beam reflects from the object surface. The second approach is to transform the signal into the frequency domain and calculate the rate of change of phase with wavelength, assuming that an essentially linear slope is directly proportional to object position. See, for example, U.S. Pat. No. 5,398,113 to Peter de Groot. This latter approach is referred to as Frequency Domain Analysis (FDA).

If a low coherence scanning interferometer is used to collect a scanning interferometry signal from a sample having a thin film (e.g., a simple single-layer partially reflective film over an opaque substrate), and if the film is sufficiently thick, then the scanning interferometry signal will include two distinct regions of fringes corresponding to the upper and lower interfaces of the film. This is shown in FIG. 1, extracted from a reference by S. Petitgrand et al. (S. Petitgrand, A. Bosseboeuf, J. P. Gilles, P. Coste, P. Nérin, P. Vabre "Mesures 3D de topographies et de vibrations à l'échelle (sub)micrométrique par microscopie optique interférométrique" Proc. Club CMOI, Méthodes et Techniques Optiques pour l'Industrie (2002). A nearly identical paper can be downloaded from Fogale Nanotech website (http://www.fogale.com/acrobat/IEFCMOI2002_FR.pdf)). According to another paper by Bosseboeuf and Petigrand (Proc. SPIE 5145, 1-16, (2003)), the distance between these two signals is "$\Delta = n_1 d$," where here $\Delta$ is the distance between the maxima of the two regions of fringe contrast, d is the physical film thickness and $n_1$ is the index of refraction.

Because the light passes through the film before reaching the substrate, there is a distortion in the apparent film thickness related to the refractive properties of the film. In prior-art references such as Bosseboeuf and Petigrand, the correction for this effect is to divide the apparent thickness by the index of refraction, to recover the true physical thickness of the film. Unfortunately, we often observe that this correction is insufficient.

In other applications, one is interested in the topology of the top and/or bottom surface of the film, instead or, or in addition to, the thickness of the thin film. Unfortunately, conventional processing of the low coherence scanning interferometry data can sometimes be corrupted by the presence of one or more underlying layers.

SUMMARY

The inventors have recognized that an accurate analysis of low coherence scanning interferometry data of a sample having one or more layers (e.g., a thin film sample) should take into account both the illumination frequency spectrum and the illumination geometry (e.g., the numerical aperture of the light used to illuminate the sample) to more accurately account for the low coherence phenomenon that produce the regions of fringe contrast. For example, in addition to the low coherence phenomenon resulting from a broadband light source, the low coherence can also result from using a high numerical aperture (NA) for directing light to, and/or receiving light from, the test object. The high NA causes light rays to contact the test surface over a range of angles, and generates different spatial frequency components in the recorded signal as the OPD is scanned. The separation of the regions of fringe contrast in a signal produced from a multilayer sample will depend on the relative strengths of such low coherence phenomena.

For example, the inventors have discovered that in the limit of very low NA and white light illumination, the apparent thickness of a thin film sample based on the separation between regions of the fringe contrast in the low coherence scanning interferometry signal is corrected by dividing this apparent thickness by the group-velocity index of refraction. In the opposite limit of very high NA and monochromatic illumination, the apparent thickness is corrected by multiplying it by the index of refraction.

For intermediate illumination conditions, where both broadband illumination and high NA contribute the localization of interference fringes, the correction of the apparent thickness based on the separation between regions of the fringe contrast can be determined based on a theoretical model (described in further detail below) that more accurately takes into account both phenomena. In practice the results of the model can be represented as a look-up table or simplified function which provides a correction factor to a user as a function of input parameters related to the illumination geometry and illumination frequency spectrum.

In another aspect, the inventors have recognized that the illumination conditions can be selected to suppress the region(s) of fringe contrast in the interferometry signal associated with an underlying layer or layers of a sample. As a result, the interferometry signal is dominated only by the fringe contrast region associated with the top surface of the sample, and subsequent processing of the interferometry signal using, for example, conventional techniques to more accurately provide surface profile information about the top surface. This phenomenon typically occurs when there is both broadband illumination (e.g., a bandwidth larger than about 100 nm in the visible) and high NA (e.g., greater than about 0.5, and preferably greater than 0.7). In certain embodiments, an objective for the low coherence scanning interferometer can be selected to provide such high NA, while also providing a low magnification (e.g., less than 10×) to provide a large field of view.

We now generally summarize different aspects and features of the invention.

In general, in one aspect, the invention features a method including: (i) providing a low coherence scanning interferometry data for at least one spatial location of a sample having multiple interfaces, wherein the data is collected using a low coherence scanning interferometer having an illumination geometry and an illumination frequency spectrum, and wherein the data includes a low coherence scanning interferometry signal having multiple regions of fringe contrast corresponding to the multiple interfaces; and (ii) determining a distance between at least one pair of interfaces based on a distance between the corresponding regions of fringe contrast and information about the illumination geometry and/or the illumination frequency spectrum.

Embodiments of the method may include any of the following features.

Determining the distance between at least a pair of the interfaces includes providing information about a correspondence between the distance between the pair of interfaces and the distance between the corresponding regions of fringe contrast in the interferometry signal for different settings of the illumination geometry and the illumination frequency spectrum. For example, the correspondence may be represented as a function or a look-up table that uses the information about the illumination geometry and/or the illumination frequency spectrum as input parameters.

The correspondence may be based on a theoretical model for the interferometer that uses the information about the illumination geometry and the illumination frequency spectrum as input parameters.

For example, the theoretical model may be based on the following expression for the interferometry signal I(ζ) as a function of scan coordinate ζ for each spatial location in the data:

$$I(\zeta) = \int_0^\infty \int_0^1 g(\beta, k, \zeta) U(\beta) V(k) \beta \, d\beta \, dk$$

where U is an illumination distribution in a pupil plane of an objective used to illuminate the sample as a function of directional cosine β, V is the illumination frequency spectrum as a function of spectral wavenumber k, and $$g(\beta,k,\zeta) = R + Z + 2\sqrt{RZ}\cos[2\beta k(h-\zeta) + (\upsilon - \omega)]$$

for a reference path reflectivity R, a sample path reflectivity Z, and a local sample height h, and where phase offsets υ, ω are system and phase change on reflection values for the reference and sample paths, respectively.

The distance between the pair of interfaces may be determined by determining an estimate for the distance between the pair of interfaces corresponding to the distance between the two regions of fringe contrast, and correcting the estimate based on the information about the illumination geometry and the frequency spectrum. For example, the correction of the initial estimate may include decreasing the estimate by a scale factor that increases with a group velocity index of the film. In another example, the correction of the initial estimate may include increasing the estimate by a scale factor that increases with a refractive index of the film.

The sample may be a thin film sample, where the pair of interfaces is a top and bottom surface of the film. The sample may have the film at some spatial locations and not others.

The sample may include a spacer element in a liquid crystal cell.

The sample may include a solder bump.

In general, in another aspect, the invention features an apparatus including: a low coherence scanning interferometer configured to collect data for at least one spatial location of a sample having at least one film, the coherence scanning interferometer having an illumination geometry and an illumination frequency spectrum, and the data including a low coherence scanning interferometry signal having multiple regions of fringe contrast corresponding to the multiple interfaces; and an electronic processor configured to analyze the data and determine a distance between at least one pair of interfaces based on a distance between the corresponding regions of fringe contrast and information about the illumination geometry and/or the illumination frequency spectrum.

Embodiments of the apparatus may include any of the following features.

The low coherence interferometer may be configured for use with an adjustable numerical aperture for the illumination geometry, and the information about the illumination geometry may include information about which numerical aperture was used to collect the interferometry signal. For example, the apparatus may further include a plurality of interference objective having different numerical apertures (NAs) each configured for use in the low coherence scanning interferometer to provide the adjustable numerical aperture for the illumination geometry.

Alternatively, or in addition, the low coherence interferometer may be configured for use with an adjustable illumination frequency spectrum, and the information about the illumination geometry may include information about which illumination frequency spectrum was used to collect the interferometry signal. For example, the apparatus may include a plurality of light sources (e.g., light emitting diodes (LEDs)) having different emission spectrums each configured for use in the low coherence scanning interferometer to provide the adjustable illumination frequency spectrum.

The electronic processor in the apparatus may also include features corresponding to those described above for the method aspect.

In general, in another aspect, the invention features a method including: using a low coherence scanning interferometer having an illumination geometry and an illumination frequency spectrum to collect a low coherence scanning interferometry signal for each of multiple spatial locations of a sample having at least one thin film with a top surface and a bottom surface; selecting the illumination geometry and the illumination frequency spectrum to suppress a region of fringe contrast in the signals corresponding to the bottom surface relative to a region of fringe contrast in the signals corresponding to the top surface; and determining a surface height profile for the top surface of the film based on the signals.

Embodiments of the method may include any of the following features.

The selected illumination geometry may include an objective to illuminate the sample with a numerical aperture greater than 0.5, or preferably greater than 0.7, or even more preferably, greater than 0.8. In some cases, the objective has a magnification less than 10× to improve the field of view.

The sample may include a spacer element in a liquid crystal cell.

The sample may include a solder bump.

In general, in another aspect, the invention features a low coherence scanning interferometer having an objective to illuminate the sample with a numerical aperture greater than 0.5 and a magnification less than 10×. For example, the numerical aperture may be greater than 0.7, or more preferably greater than 0.8.

Unless otherwise defined, all technical and scientific terms used herein have the same meaning as commonly understood by one of ordinary skill in the art to which this invention belongs. In case of conflict with publications, patent applications, patents, and other references mentioned incorporated herein by reference, the present specification, including definitions, will control.

Other features, objects, and advantages of the invention will be apparent from the following detailed description.

BRIEF DESCRIPTION OF THE DRAWINGS

FIGS. 6(a) and 6(b) show simulations of a low-coherence scanning interferometry signal based on the model disclosed herein for a 2-μm thick film of index 2 deposited on a substrate of index 4, viewed with a 500-nm center wavelength. FIG. 6(a) is for a broad 200-nm gaussian bandwidth, and narrow 0.28 NA illumination. FIG. 6(b) is for a narrow 5-nm bandwidth, and wide 0.80 NA illumination.

FIGS. 11a and 11b show the structure before and after planarization, respectively.

FIG. 12a shows the structure before addition of solder. FIG. 12b shows the structure after addition of solder but prior to flowing the solder.

Like reference numerals in different drawings refer to common elements.

DETAILED DESCRIPTION

Figure 2:
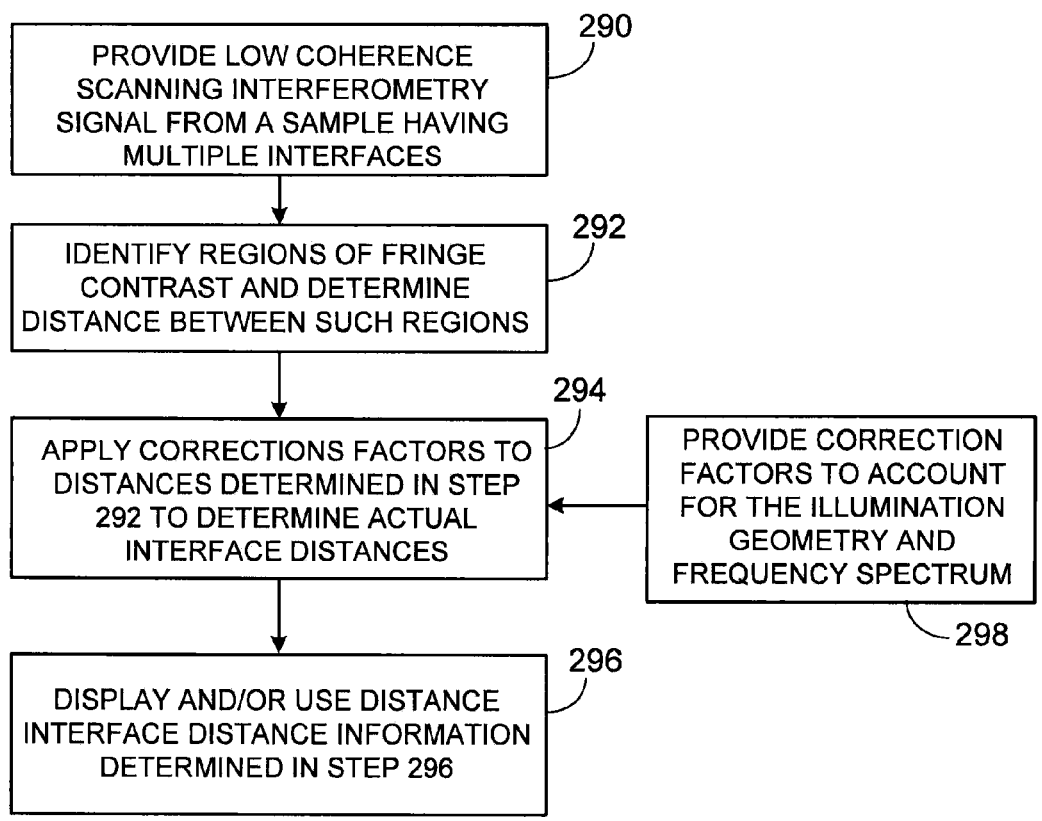
FIG. 2 is a flow chart showing an interferometry method for determining a thickness of a layer in a sample having one or more layers.

The invention features a method to accurately correct the distortion in the apparent film thickness as measured by a low-coherence interference microscope by taking into account the coherence effects related to the illumination geometry. In preferred embodiments, the correction can be by means of a formula or look up table based in part on the NA of the objective and the nominal spectral characteristics of the source light. FIG. 2 is flow chart providing an exemplary sequence of steps for the method.

In step 290, an interference microscope provides a scanning interference signal from each of different surface locations of a sample having one or more layers. The interference microscope is a low-coherence (spectrally broadband and/or extended source) interferometer. The interferometer is used to mechanically or electro-optically scan the optical path difference (OPD) between a reference and measurement path, the measurement path being directed to an object surface. For example, scanning an interference objective along the line of the surface height coordinate generates an interference signal with a localized fringe contrast. A computer records an interference intensity signal during the OPD scan for each of multiple camera pixels corresponding to the different surface locations of the sample. The apparatus is configured to analyze surfaces that may have one or more layers (e.g., a partially reflective thin film on a substrate) for which multiple interference signals are generated in sequence during the scan, corresponding to the interfaces at the surface and between layers.

In step 292, the scanning interference signal from the different locations are analyzed to identify regions of fringe contrast associated with each reflective or partially reflective interface in the sample. Typically, this done computationally. The center location of each region of fringe contrast can be identified using conventional methods, such as identifying the peak in the fringe contrast envelope, identifying the centroid of the fringe, or using frequency domain analysis (FDA). For example, when using FDA, each of region of fringe contrast is Fourier transformed and the center of each fringe contrast region is determined from the slope of the phase of the Fourier transform with respect to wavevector. In further embodiments, techniques that account for system dispersion characteristics can be used to more accurately determine the fringe contrast positions in the scanning interferometry data. Suitable techniques are disclosed in U.S. patent application Ser. No. 10/941,651 entitled "SURFACE PROFILING USING AN INTERFERENCE PATTERN MATCHING TEMPLATE" by Peter J. de Groot and filed Sep. 15, 2004, the contents of which are incorporated herein by reference. The center position of each region of fringe contrast in the scanning interferometry signal provide an initial estimate for the relative position of each reflective or partially reflective interface in the sample.

In step 294, correction factors are applied to the estimates determined in step 292, to more accurately determine the physical distance between the interfaces of the relevant film layer (e.g., the actual thickness of a thin film layer). For example, the correction factor can be a scaling factor that converts the scanning distance between respective regions of fringe contrast extracted in step 292 to the physical distance between the interfaces of the relevant film layer. The correction factor can be applied to the scanning distances for each spatial location in the interferometry data to provide a thickness profile for each layer of the sample. Also, the thicknesses determined for different spatial locations can be averaged to improve signal-to-noise. Furthermore, the data extracted in step 292 can be laterally smoothed before applying the correction factor(s) and/or determining the thickness measurement(s).

In step 296, the resulting thickness value(s) or profile(s) can shown on a user display and/or directed to another process as part of a quality control feedback loop (e.g., to determine whether, for example, a chemical mechanical processing step, solder bump thickness, or liquid crystal spacer thickness, has been optimized).

The correction factors themselves are determined in step 298, based on input parameters that include the geometric and spectral characteristics (i.e., the illumination geometry and illumination frequency spectrum) of the instrument used to collect the data in step 290. The input parameters may also include the refractive index dispersion of the film layers. The correction factors may be based on direct calculations using a theoretical model for the low coherence interferometry signal (which is described further below). Alternatively, the correction factors may be determined from a look-up table or simplified function that is based on the theoretical model for typical values of the illumination geometry and illumination frequency spectrum for the interferometer used to collect the data in step 290. Whatever the exact implementation, the correction factors provide a correspondence between the distances extracted in step 292, which are related to the scanning distances between the different regions of fringe contrast, and the actual distances between different interfaces of the sample (e.g., a thickness of a thin film) as a function of the experimental conditions used to collect the data in step 290, including at least the optical spectrum and the illumination geometry as input parameters.

For example, in the limit of very low NA and white light illumination, the correction approaches dividing the apparent thickness given by the scanning distance in step 292 by the group-velocity index of refraction. In the opposite limit, of very high NA and monochromatic illumination, the correction approaches multiplying the apparent thickness given by the scanning distance in step 292 by the index of refraction.

The interferometer in step 290 may include any of the following features: a spectrally narrow-band light source with a high numerical aperture (NA) objective; a spectrally broad band light source; a combination of a high NA objective and a spectrally broadband source; an interferometric microscope objectives, including oil/water immersion and solid immersion types, in e.g. Michelson, Mirau or Linnik geometries; a sequence of measurements at multiple wavelengths; unpolarized light; and polarized light, including linear, circular, or structured. For example, structured polarized light may involve, for example, a polarization mask, generating different polarizations for different segments of the illumination or imaging pupils, so as to reveal polarization-dependent optical effects attributable to surface characteristics.

Figure 3:
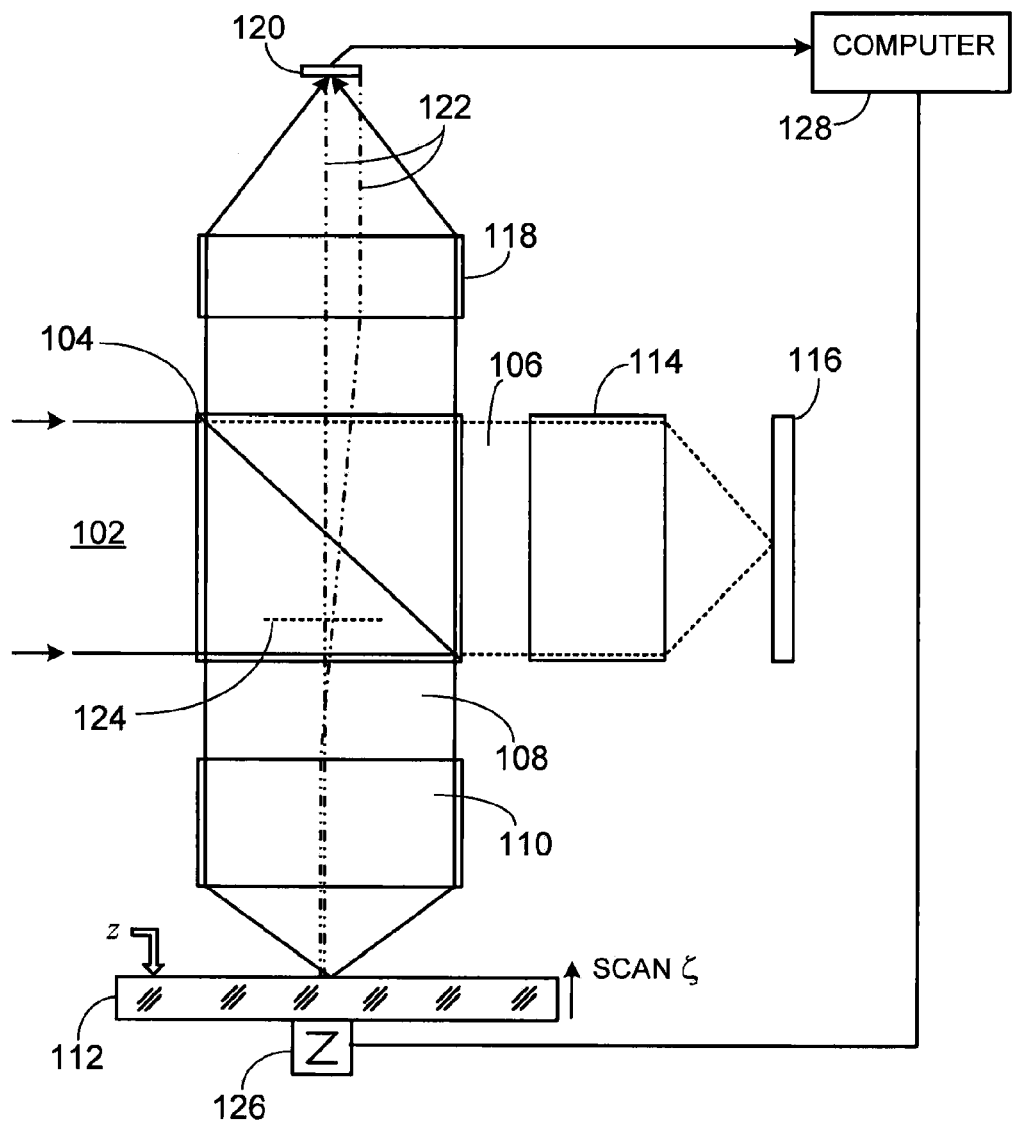
FIG. 3 is a schematic drawing of a Linnik-type scanning interferometer.

FIG. 3 shows a scanning interferometer of the Linnik type. Illumination light 102 from a source (not shown) is partially transmitted by a beam splitter 104 to define reference light 106 and partially reflected by beam splitter 104 to define measurement light 108. The measurement light is focused by a measurement objective 110 onto a test sample 112 (e.g., a sample comprising a thin single- or multi-layer film of one or more dissimilar materials). Similarly, the reference light is focused by a reference objective 114 onto a reference mirror 116. Preferably, the measurement and reference objectives have common optical properties (e.g., matched numerical apertures). Measurement light reflected (or scattered or diffracted) from the test sample 112 propagates back through measurement objective 110, is transmitted by beam splitter 104, and imaged by imaging lens 118 onto a detector 120. Similarly, reference light reflected from reference mirror 116 propagates back through reference objective 114, is reflected by beam splitter 104, and imaged by imaging lens 118 onto a detector 120, where it interferes with the measurement light.

For simplicity, FIG. 3 shows the measurement and reference light focusing onto particular points on the test sample and reference mirror, respectively, and subsequently interfering on a corresponding point on the detector. Such light corresponds to those portions of the illumination light that propagate perpendicular to the pupil planes for the measurement and reference legs of the interferometer. Other portions of the illumination light ultimately illuminate other points on the test sample and reference mirror, which are then imaged onto corresponding points on the detector. In FIG. 3, this is illustrated by the dashed lines 122, which correspond to the chief rays emerging from different points on the test sample that are imaged to corresponding points on the detector. The chief rays intersect in the center of the pupil plane 124 of the measurement leg, which is the back focal plane of measurement objective 110. Light emerging from the test sample at an angle different from that of the chief rays intersect at a different location of pupil plane 124.

In preferred embodiments, detector 120 is a multiple element (i.e., multi-pixel) camera to independently measure the interference between the measurement and reference light corresponding to different points on the test sample and reference mirror (i.e., to provide spatial resolution for the interference pattern).

A scanning stage 126 coupled to test sample 112 scans the position of the test sample relative to measurement objective 110, as denoted by the scan coordinate $\zeta$ in FIG. 3. For example, the scanning stage can be based on a piezoelectric transducer (PZT). Detector 120 measures the intensity of the optical interference at one or more pixels of the detector as the relative position of the test sample is being scanned and sends that information to a computer 128 for analysis.

Because the scanning occurs in a region where the measurement light is being focused onto the test sample, the scan varies the optical path length of the measurement light from the source to the detector differently depending on the angle of the measurement light incident on, and emerging from, the test sample. As a result, the optical path difference (OPD) from the source to the detector between interfering portions of the measurement and reference light scale differently with the scan coordinate $\zeta$ depending on the angle of the measurement light incident on, and emerging from, the test sample. In other embodiments of the invention, the same result can be achieved by scanning the position of reference mirror 116 relative to reference objective 114 (instead of scanning test sample 112 relative to measurement objective 110).

This difference in how OPD varies with the scan coordinate ζ introduces a limited coherence length in the interference signal measured at each pixel of the detector. For example, the interference signal (as a function of scan coordinate) is typically modulated by an envelope having a spatial coherence length on the order of $\lambda/2\,(NA)^2$, where $\lambda$ is the nominal wavelength of the illumination light and NA is the numerical aperture of the measurement and reference objectives. To increase the limited spatial coherence, the objectives in the scanning interferometer preferably define a large numerical aperture, e.g., greater than about 0.7 (or more preferably, greater than about 0.8, or greater than about 0.9). The interference signal can also be modulated by a limited temporal coherence length associated with the spectral bandwidth of the illumination source. Depending on the configuration of the interferometer, one or the other of these limited coherence length effects may dominate, or they may both contribute substantially to the overall coherence length.

Figure 4:
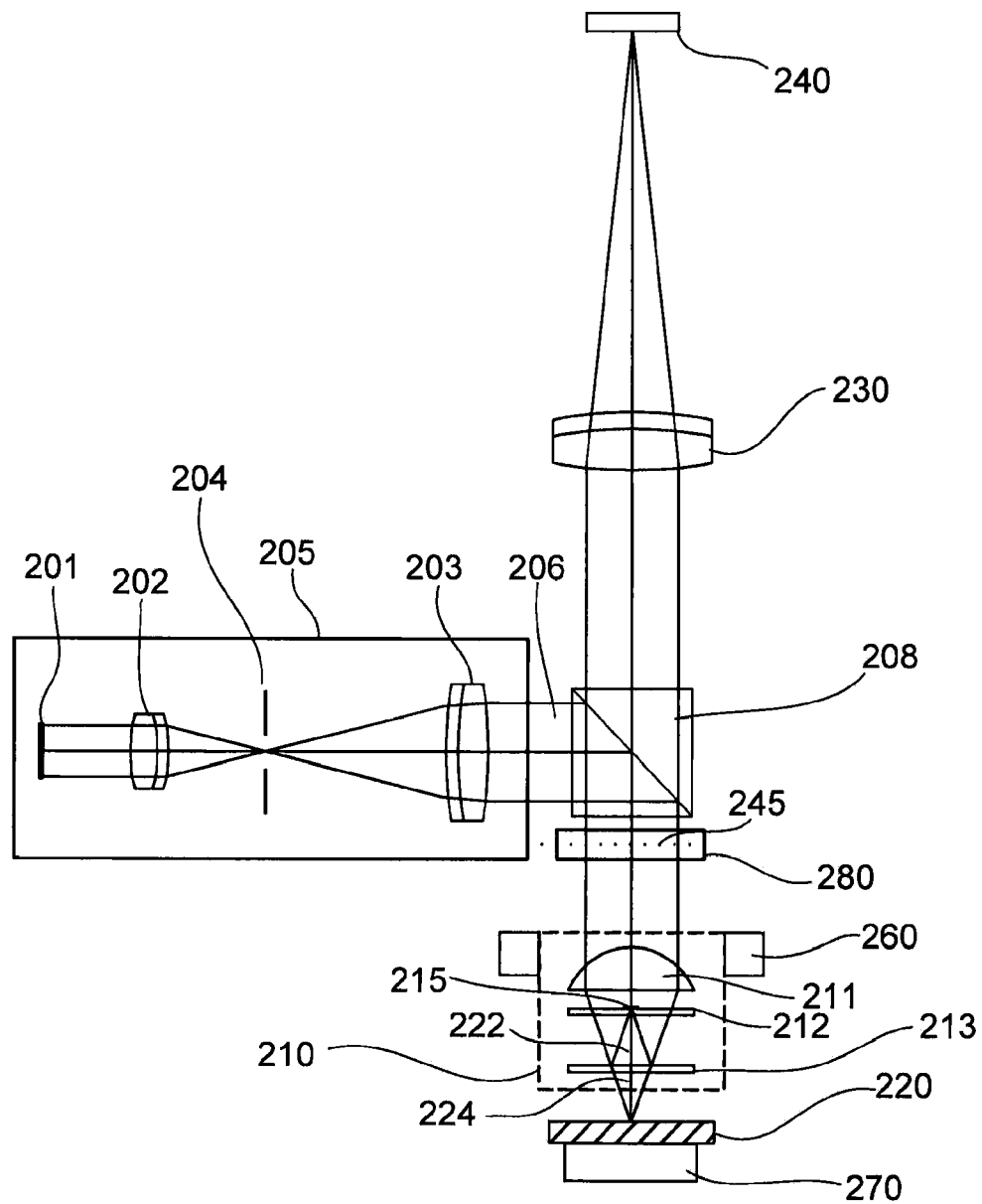
FIG. 4 is a schematic drawing of a Mirau-type scanning interferometer.

Another example of a scanning interferometer is the Mirau-type interferometer shown in FIG. 4.

Referring to FIG. 4, a source module 205 provides illumination light 206 to a beam splitter 208, which directs it to a Mirau interferometric objective assembly 210. Assembly 210 includes an objective lens 211, a reference flat 212 having a reflective coating on a small central portion thereof defining a reference mirror 215, and a beam splitter 213. During operation, objective lens 211 focuses the illumination light towards a test sample 220 through reference flat 212. Beam splitter 213 reflects a first portion of the focusing light to reference mirror 215 to define reference light 222 and transmits a second portion of the focusing light to test sample 220 to define measurement light 224. Then, beam splitter 213 recombines the measurement light reflected (or scattered) from test sample 220 with reference light reflected from reference mirror 215, and objective 211 and imaging lens 230 image the combined light to interfere on detector (e.g., a multi-pixel camera) 240. As in the system of FIG. 3, the measurement signal(s) from the detector is sent to a computer (not shown).

The scanning in the embodiment of FIG. 4 involves a piezoelectric transducer (PZT) 260 coupled to Mirau interferometric objective assembly 210, which is configured to scan assembly 210 as a whole relative to test sample 220 along the optical axis of objective 211 to provide the scanning interferometry data $I(\zeta,h)$ at each pixel of the camera. Alternatively, the PZT may be coupled to the test sample rather than assembly 210 to provide the relative motion there between, as indicated by PZT actuator 270. In yet further embodiments, the scanning may be provided by moving one or both of reference mirror 215 and beam splitter 213 relative to objective 211 along the optical axis of objective 211.

Figure 1:
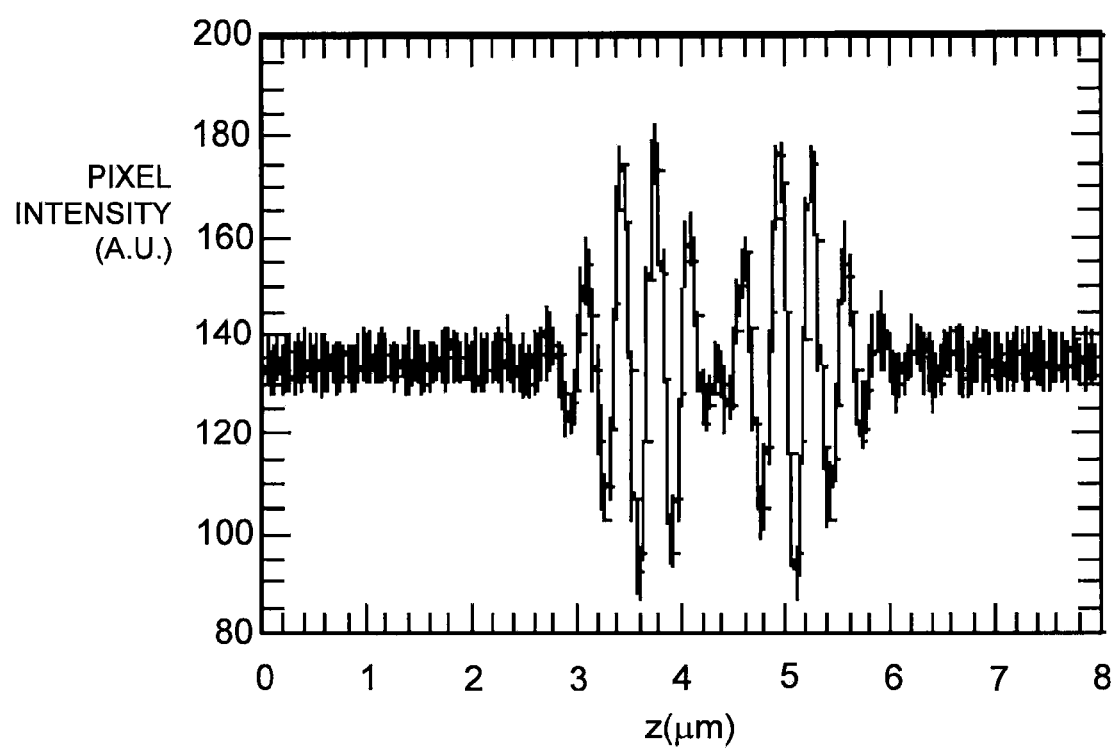
FIG. 1 is a graph showing a typical low coherence interferometry signal for a thin film sample.

Source module 205 includes a spatially extended source 201, a telescope formed by lenses 202 and 203, and a stop 204 positioned in the front focal plane of lens 202 (which coincides with the back focal plane of lens 203). This arrangement images the spatially extended to source onto the pupil plane 245 of Mirau interferometric objective assembly 210, which is an example of Koehler imaging. The size of stop controls the size of the illumination field on test sample 220. In other embodiments, the source module may include an arrangement in which a spatially extended source is imaged directly onto the test sample, which is known as critical imaging. Either type of source module may be used with the Linnik-type scanning interferometry system of FIG. 1.

In much of the analysis herein, it is assumed that the polarization state of the light in the pupil plane is random, i.e., comprised of approximately equal amounts of both s polarizations (orthogonal to the plane of incidence) and p (orthogonal to the plane of incidence) polarizations. Alternative polarizations are possible, including pure s polarization, such as may be realized by means of a radial polarizer placed in the pupil plane (e.g., in the back-focal plane of the measurement object in the case of a Linnik interferometer and in the back focal plane of the common objective in the Mirau interferometer). Other possible polarizations include radial p polarization, circular polarization, and modulated (e.g. two states, one following the other) polarization for ellipsometric measurements. In other words, optical properties of the test sample can be resolved not only with respect to their angle- or wavelength-dependence, but also with respect to their polarization dependence or with respect to a selected polarization. Such information may also be used to improve the accuracy of thin film structure characterization.

To provide such ellipsometry measurements, the scanning interferometry system may include a fixed or variable polarizer in the pupil plane. Referring again to FIG. 4, the Mirau-type interferometry system, for example, includes polarization optics 280 in the pupil plane to select a desired polarization for the light incident on, and emerging from the test sample. Furthermore, the polarization optics may be reconfigurable to vary the selected polarization. The polarization optics may include one or more elements including polarizers, waveplates, apodization apertures, and/or modulation elements for selecting a given polarization. Furthermore, the polarization optics may be fixed, structured or reconfigurable, for the purpose of generating data similar to that of an ellipsometer. For example, a first measurement with a radially-polarized pupil for s polarization, followed by a radially-polarized pupil for p polarization. In another example, one may use an apodized pupil plane with linearly polarized light, e.g., a slit or wedge, which can be rotated in the pupil plane so as to direct any desired linear polarization state to the object, or a reconfigurable screen such as a liquid crystal display.

We now describe a theoretical model for the scanning interferometry signal. The model is the basis for providing the correction factors in step 298 of FIG. 2.

Figure 5:
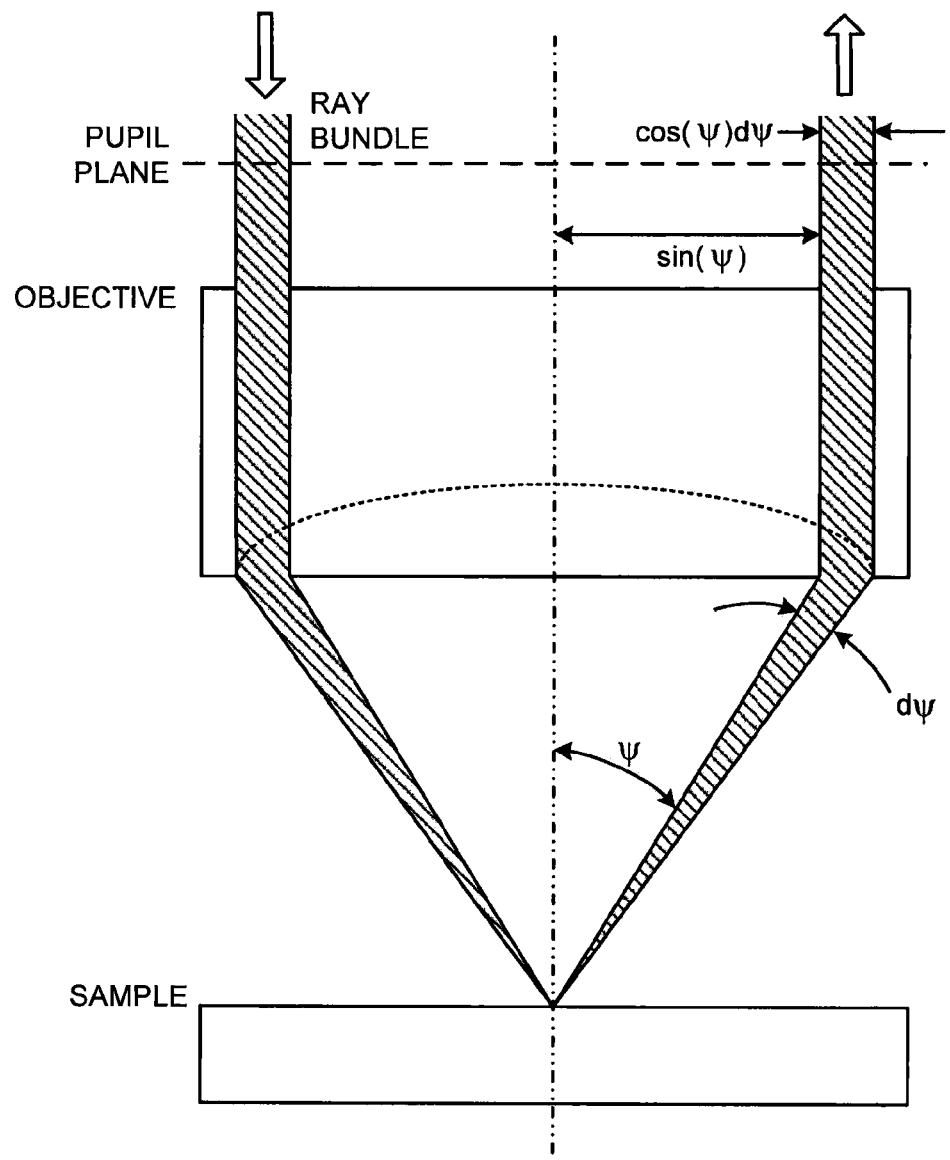
FIG. 5 is a diagram showing illumination of the test sample through an objective lens.

A full physical model can be very elaborate, taking into account the partial coherence of the light source, polarization mixing in the interferometer, the imaging properties of high-NA objectives, and the interaction of electric field vectors at high angles of incidence and in the presence of discontinuous surface features. We elect here to simplify the model by assuming a randomly-polarized, low-coherence extended source and a smooth surface that does not scatter or diffract incident light. The total signal is the incoherent sum of the interference contributions of all of the ray bundles passing through the pupil plane of the objective and reflecting from the object surface at an incident angle ψ, as shown in FIG. 5.

Following the usual two-beam interference analysis, the interference contribution for a single ray bundle through the optical system is proportional to $$g(\beta,k,\zeta) = R + Z + 2\sqrt{RZ}\cos[2\beta k(h-\zeta)+(\upsilon-\omega)], \quad (1)$$

where Z is the effective object intensity reflectivity, including e.g. the transmissivity of the beamsplitter, and R is the effective reference reflectivity, including both the beamsplitter and the reference mirror, and we assume a refractive index of 1 for the ambient medium. The directional cosine β for an incident angle ψ is $$\beta = \cos(\psi) \quad (2)$$

and the angular wavenumber k for a source wavelength λ is $$k = (2\pi/\lambda) \quad (3)$$

The phase term in Eq. (1) has a contribution ω for the object path in the interferometer, including any phase change on reflection from the object surface (including underlying layer(s)), and a contribution υ for the reference path, including the reference mirror and other optics in the objective. In the general case, Z, R, υ, ω all vary with directional cosine β and angular wavenumber k.

The total interference signal for a single scan position ζ is the integral over all points in the pupil plane and over all wavelengths for the ray bundle contributions g (β,k,ζ):

$$I(\zeta) = \int_0^\infty \int_0^1 g(\beta, k, \zeta) U(\beta) V(k) \beta \, d\beta \, dk \tag{4}$$

where U (β) is the intensity distribution in the pupil plane of the objective and V (k) is the optical spectrum distribution. The extra weighting factor β in Eq. (4) follows from a cos(ψ) term attributable to the projection angle and a sin(ψ) term for the diameter of the annulus of width dψ in the pupil plane:

$$\cos(\psi)\sin(\psi)d\psi = -\beta d\beta \tag{5}$$

We assume that the objective obeys the Abbé sine condition as shown in FIG. 5.

Certain simplifying assumptions often permit direct evaluation of Eq. (4). The most common simplification is to assume a point source in the center of the pupil plane (U=0 for β≠0), equivalent to a very low NA illumination, and a gaussian spectrum. In the more general case of an extended source and a more complicated source spectrum, Eq. (4) implies a numerical integration.

In preferred embodiments, the modeling can be further simplified by frequency analysis to produce a more computationally efficient way of simulating the interference intensity signal I(ζ). For most applications of interest in common height-scanning interferometric microscopes, the most rapidly varying factor in the integrand of Eq. (4) as a function of k and β is the quasi-periodic interference contribution g (β,k, ζ). This factor in turn is modulated most rapidly by the product 2βk in the phase term, which we can redefine physically as the spatial frequency $\hat{\kappa}$ of the interference contribution g(β, k,ζ) generated by scanning orthogonally to the sample surface:

$$\hat{\kappa} = 2\beta k \tag{6}$$

This spatial frequency $\hat{\kappa}$ is the angular rate of change of the phase term of g(β,k,ζ) as a function of the scan coordinate ζ. In the integration, various combinations of β and k result in the same spatial frequency $\hat{\kappa}$. One path to simplifying Eq. (4), therefore, is to recast the calculation in terms equivalent to these spatial frequencies. As we shall show, the numerical calculation of the intensity signal I(ζ) can then be more efficiently expressed as a fast Fourier Transform of the frequency-domain spectrum q(K) of the signal, where K is the frequency coordinate of the transformed data.

The first step in the simplifying analysis is the somewhat counter-intuitive step of Fourier Transforming Eq. (4), leading to a triple integral that defines q (K):

$$q(K) = \int_0^\infty \int_0^1 U(\beta) V(k) \left\{ \int_{-\infty}^\infty g(\beta, k, \zeta) \exp(iK\zeta) \, d\zeta \right\} \beta \, d\beta \, dk \tag{7}$$

After expansion of the cosine term in g(β,k,ζ) in the usual way $$2\cos(\hat{\kappa}\zeta + \ldots) = \exp(i\hat{\kappa}\zeta + \ldots) + \exp(-i\hat{\kappa}\zeta - \ldots) \tag{8}$$

and using the Dirac delta function $$\delta(K \pm \hat{\kappa}) = \int_{-\infty}^\infty \exp[(K \pm \hat{\kappa})i\zeta] \, d\zeta, \tag{9}$$

the inner integral over ζ evaluates to $$\int_{-\infty}^\infty g(\beta, k, \zeta) \exp(iK\zeta) \, d\zeta = \tag{10}$$

$$\delta(K)(R + Z) + \delta(K - \hat{\kappa})\sqrt{RZ} \exp[i\hat{\kappa}h + i(\upsilon - \omega)] +$$

$$\delta(K + \hat{\kappa})\sqrt{RZ} \exp[-i\hat{\kappa}h - i(\upsilon - \omega)]$$

The δ functions underscore that the mathematically general frequencies K of the Fourier decomposition relate to the spatial frequency $\hat{\kappa}$ defined by Eq. (6). A logical change of variables in Eq. (7) for the second inner integral at constant k is therefore $$\beta = \hat{\kappa}/2k \tag{11}$$

$$d\beta = d\hat{\kappa}/2k \tag{12}$$

Eq. (7) after using Eq. (10) then becomes $$q(K) = \int_0^\infty \int_0^{2k} \delta(K)(R + Z) \Gamma \, d\hat{\kappa} \, dk + \tag{13}$$

$$\int_0^\infty \int_0^{2k} \delta(K - \hat{\kappa})\sqrt{RZ} \exp[i\hat{\kappa}h + i(\upsilon - \omega)] \Gamma \, d\hat{\kappa} \, dk +$$

$$\int_0^\infty \int_0^{2k} \delta(K + \hat{\kappa})\sqrt{RZ} \exp[-i\hat{\kappa}h - i(\upsilon - \omega)] \Gamma \, d\hat{\kappa} \, dk$$

where we have gathered the weighting terms as $$\Gamma(\hat{\kappa},k) = U[\beta(\hat{\kappa},k)] V(k) \hat{\kappa}/4k^2. \tag{14}$$

Although for compactness we have not noted the dependencies explicitly in Eq. (13), it is understood that Z, R, υ, ω, Γ all vary with spatial frequency $\hat{\kappa}$ and wavelength k.

The presence of dirac functions in the integrands of Eq. (13) eventually leads to the following simplification:

$$q(K) = \delta(K) \int_0^\infty \int_{K/2}^\infty (R + Z) \Gamma \, dk \, d\hat{\kappa} + \tag{15}$$

$$H(K)\exp(iKh) \int_{K/2}^\infty \{\sqrt{RZ} \exp[i(\upsilon - \omega)] \Gamma\}_{\hat{\kappa} = +K} dk +$$

$$H(-K)\exp(-iKh) \int_{-K/2}^\infty \{\sqrt{RZ} \exp[-i(\upsilon - \omega)] \Gamma\}_{\hat{\kappa} = -K} dk.$$

where H is the unitless Heaviside step function defined by $$H(u) = \begin{cases} 0 & \text{for } u < 0 \\ 1 & \text{otherwise} \end{cases} \tag{16}$$

The calculation of the frequency-domain representation of the interference signal has now been reduced to one double integral for the DC term (K=0), and to single integrals over k for all other spatial frequencies (K≠0). This is a substantial simplification in terms of the number of numerical evaluations.

The incoherent superposition model accommodates polarization by summing the resulting Fourier components q(K) for s and p polarization contributions. Writing this explicitely for fully random polarization, $$q(K)=q_s(K)+q_p(K), \quad (17)$$

where the s and p subscripts in Eq. (17) refer to Eq. (15) with all of the relevant parameters calculated for the corresponding polarization state, including the sample reflectivity, the beamsplitter, and so on.

The final calculation of the interference signal is now an inverse Fourier Transform $$I(\zeta) = \int_{-\infty}^{\infty} q(K)\exp(-iK\zeta)\,dK \quad (18)$$

Although this is another integral, it can be evaluated by a numerical FFT and is therefore of low computational burden.

One benefit of Eq. (15) is computational efficiency. To illustrate this, the integrals are replaced with sums as follows:

$$q_0 = \sum_{k\geq 0}\sum_{k>K/2} (R+Z)\Gamma \quad (19)$$

$$\ldots$$

$$q(K>0) = \exp(iKh)\sum_{k>K/2} \sqrt{RZ}\exp[i(\upsilon-\omega)]\Gamma. \quad (20)$$

If the N discrete samples for I(ζ) are spaced by an increment $\zeta_{step}$, there will be N/2+1 positive spatial frequencies starting from zero and rising to N/2 cycles per data trace, spaced by an increment $$K_{step} = \frac{2\pi}{N\zeta_{step}}. \quad (21)$$

Unless the spectral bandwidth and or the range of incident angles is exceptionally large, only a fraction of the total frequency range is needed to fully characterize the signal. There are therefore only a few relevant K values for which q(K) is nonzero. For example, if we acquire data at a nominal rate of eight camera frames per interference fringe, this is a spatial frequency of N/8 cycles per data trace in a numerical FFT. Assuming quite safely that the source bandwidth is no greater than the nominal mean wavelength itself, there would be <N/8 values to calculate using Eq. (20). In the example following Eq. (5), if there are N=256 individual scan positions, the number of relevant K values will be 32, and if we employ 64 angular wavenumbers k in the numerical integration, there are 2048 calculations each for Eqs. (19) and (20), or of order 200× fewer complex calculations then a direct numerical evaluation of Eq. (4). Even after factoring in the cost of the inverse Fourier Transform, this substantial relief in computation makes it more practical to perform full-field simulations of signals in low coherence interferometry.

It is worthwhile considering the limit cases of collimated white light (temporal coherence limit) and high-NA monochromatic illumination (spatial coherence limit). Along with verifying Eq. (13), these limit cases provide insight into the frequency-domain portrait of the interference signal.

For both of these limit cases, as a first simplifying step, let us assume that the phase contribution (υ−ω)=0 for all K, k and that the reflectivities R, Z are independent of incident angle and wavelength, so that the integrals in Eq. (13) simplify to $$q(K) = \delta(K)(R+Z)\int_0^\infty \int_{K/2}^\infty \Gamma(\hat{k},k)\,dk\,d\hat{k} + \quad (22)$$
$$H(K)\exp(iKh)\sqrt{RZ}\int_{K/2}^\infty \Gamma(K,k)\,dk +$$
$$H(-K)\exp(-iKh)\sqrt{RZ}\int_{-K/2}^\infty \Gamma(-K,k)\,dk$$

Now we have only to handle integrals involving the weighting factor Γ($\hat{k}$,k) defined in Eq. (14).

One limit case is for collimated white light. The illumination angle for this case is ψ=0 and consequently the pupil plane function is $$U(\beta)=\delta(\beta-1). \quad (23)$$

Rewriting in terms of k, $$U(K,k)=\delta(K/2k-1). \quad (24)$$

Using the mathematical identity $$\delta[f(k)] = \frac{\delta(k-\xi)}{|df/dk|_{k=\xi}} \quad (25)$$

where ξ is the root of f(k), we have $$\Gamma(K,k) = \frac{K^2}{8}\frac{V(k)}{k^2}\delta(k-K/2). \quad (26)$$

The integrals simplify via the delta function to $$q(K) = \delta(K)\frac{(R+Z)}{2}\int_0^\infty V(\hat{k}/2)\,d\hat{k} + H(K)\frac{\sqrt{RZ}\exp(iKh)}{2}V(K/2) + \quad (27)$$
$$H(-K)\frac{\sqrt{RZ}\exp(-iKh)}{2}V(-K/2).$$

Looking at the positive, nonzero portion of the spectrum, we see that the magnitude of the Fourier coefficients are directly proportional to the source spectral distribution V:

$$|q(K>0)|\propto V(k) \quad (28)$$

where at normal incidence the frequency K is twice the angular wavenumber k:k=K/2. Eq. (28) is the familiar result that there is a Fourier transform relationship between the interference signal and the emission spectrum of the white light source.

The opposing limit is an extended monochromatic light source. This may be represented by a delta-function spectrum for a nominal angular wavenumber $k_0$:

$$V(k)=\delta(k-k_0). \quad (29)$$

Eq. (22) readily simplifies to $$q(K) = \delta(K)(R+Z)\int_0^\infty \hat{\kappa} U(\hat{\kappa}/2k_0)\,d\hat{\kappa} + \qquad (30)$$

$$H(K)H(k_0-K/2)\frac{\exp(iKh)\sqrt{RZ}}{4k_0^2}KU(K/2k_0) +$$

$$H(-K)H(k_0+K/2)\frac{\exp(-iKh)\sqrt{RZ}}{4k_0^2}KU(-K/2k_0)$$

Looking once again at the positive, nonzero portion of the spectrum, we see that the magnitude of the Fourier coefficients are now proportional to the function U weighted by the spatial frequency K:

$$|q(K>0)| \propto \beta U(\beta) \qquad (31)$$

where the spatial frequency K is proportional to the directional cosine $\beta$: $\beta = K/2k_0$. This reveals a Fourier transform relationship between the interference signal and the cosine of the illumination angle.

Most successful interference microscope profilometry applications today are for single material surfaces. For these cases, using the Fresnel equations, one can calculate an amplitude reflectivity z that for the simplest case of an ideal beamsplitter fully defines the reflectivity Z and phase shift $\omega$ for the measurement path:

$$Z(\beta,k) = |z(\beta,k)|^2 \qquad (32)$$

$$\omega(\beta,k) = arg[z(\beta,k)] \qquad (33)$$

Here again, the incoherent superposition model accommodates the dependency of the reflection coefficient z on polarization by summing the resulting Fourier components for s and p polarization contributions (Eq. (17)).

A more challenging situation for an interference microscope is an object comprised of partially-transparent thin film layers. Such samples are being delivered with increasing frequency to the optical metrology lab as thin film nanostructures such as MEMS devices, flat panel display pixels, and patterned semiconductors extend their dominance in high technology applications.

A straightforward example is a single-layer film deposited on a substrate. The amplitude reflectivity z becomes $$z(\beta,k) = \frac{\vartheta + \vartheta' \exp[2ikL\beta'(\beta)n']}{1 + \vartheta\vartheta' \exp[2ikL\beta'(\beta)n']} \qquad (34)$$

where L is the thickness of the film, n' is the index of the film, $\theta$ is the reflectivity of the air-film interface, $\theta'$ is the reflectivity of the film-substrate interface, and $$\beta'(\beta) = \sqrt{1-(1-\beta^2)/n'^2}. \qquad (35)$$

is the directional cosine of propagation within the film.

The model can be similarly extended to structures with multiple films.

The interference signal generation for a thin film is quite interesting and has some surprises, especially with high-NA objectives. FIGS. 6(a) and 6(b) compares computer simulations of the model of an interference microscope for a L=2-μm layer of a hypothetical dielectric film of index n'=2 on a substrate of index 4. FIG. 6(a) shows that with the white light illumination, there are two distinct signals corresponding to the two interfaces. The film appears to be twice the physical thickness L, the optical thickness being close to Ln'. The signals are well separated and one can analyze each of them separately to determine the profile of each interface. In prior-art systems, the technique for finding the physical thickness is to divide by the index of refraction n'. The model shows, however, that the correction is more accurately the group velocity index $n'_G$ of the film material, which takes into account the dispersion in the material. Note that the group velocity index is defined as the derivative of the wavenumber with respect to frequency. The distinction can be very important. For example, if the film is common silicon dioxide, using the group velocity index as proposed herein improves the measurement accuracy with respect to the prior art by 4%.

FIG. 6(b) shows that for monochromatic light and a high-NA objective, there are again two signals, but this time they are much closer together than in FIG. 6(a), the optical thickness being close to L/n'. Here the apparent thickness is actually inferior to the physical thickness by about a factor of two. Use of the prior-art Ln' formula in this case would lead to an even more serious error in determining the correct physical thickness.

Figure 7A:
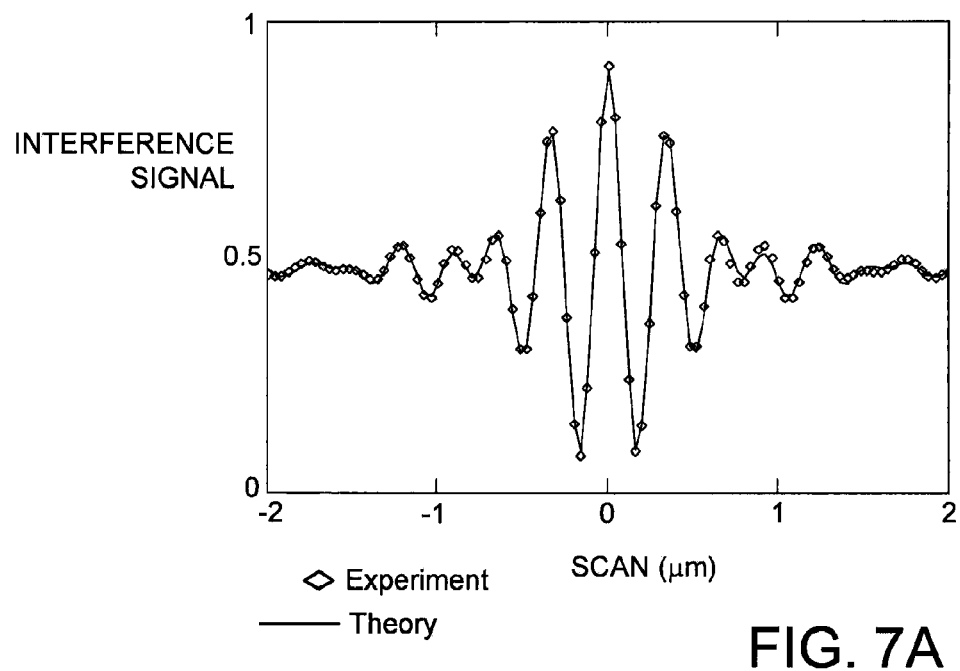
FIG. 7(a) is a graph showing agreement between the interferometry signal predicted by the model and experimental data for a SiC flat.

We have also verified the model experimentally. We viewed a solid-surface, SiC flat using a 100×, 0.78 NA Mirau objective in a microscope with a white-light LED having a 62-nm emission bandwidth. We assumed (and attempted experimentally) a uniform illumination of the pupil, thus $U(\beta)=1$ within the NA of the objective and outside the central Mirau obscuration, and is zero elsewhere. The interference objective was treated as having a perfect 50/50 beamsplitter with a fixed value for the reference path phase shift $\upsilon$, and we allowed the signal strength and an average value of the phase offset $\omega$ to be adjustable parameters in comparing experiment to theory. FIG. 7(a) shows excellent agreement with experimental data, indicating that the simple incoherent superposition model is sufficient for simulating the main features of interference signals in practical applications.

Figure 7B:
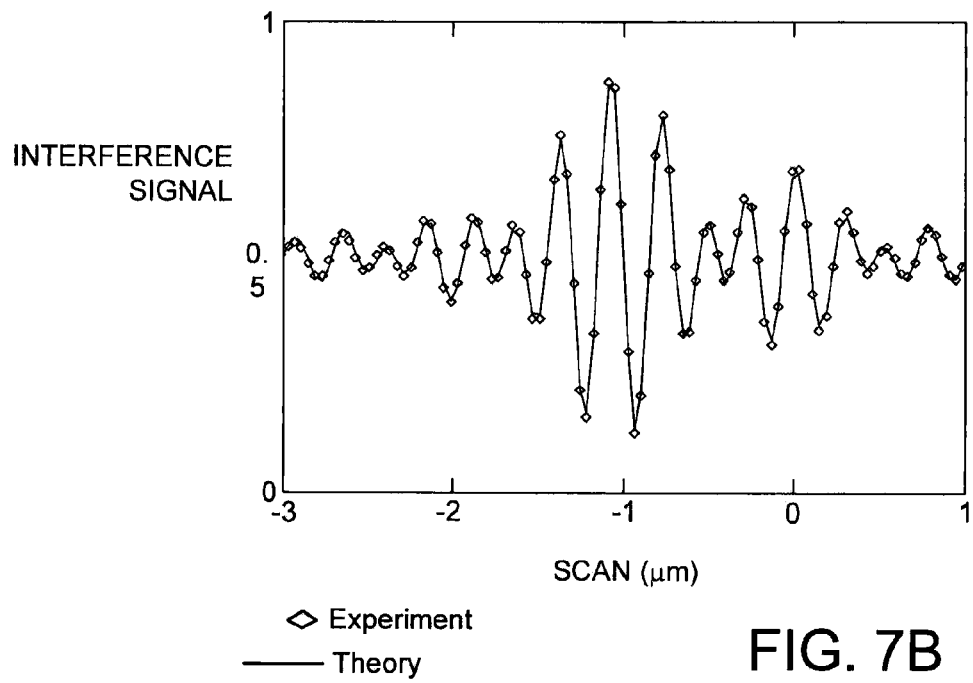
FIG. 7(b) is a graph showing agreement between the interferometry signal predicted by the model and experimental data for a thin film standard of 1025 nm of $SiO_2$ on Si.
Figure 8A:
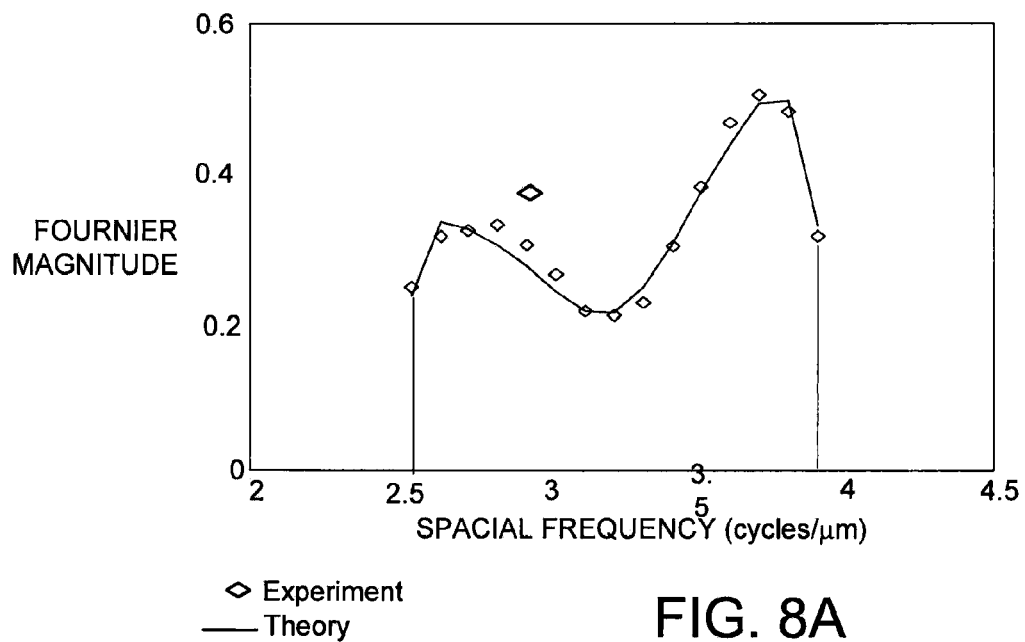
FIGS. 8(a) and 8(b) are graphs showing the agreement of the data in FIG. 7(b) in the frequency domain.
Figure 8B:
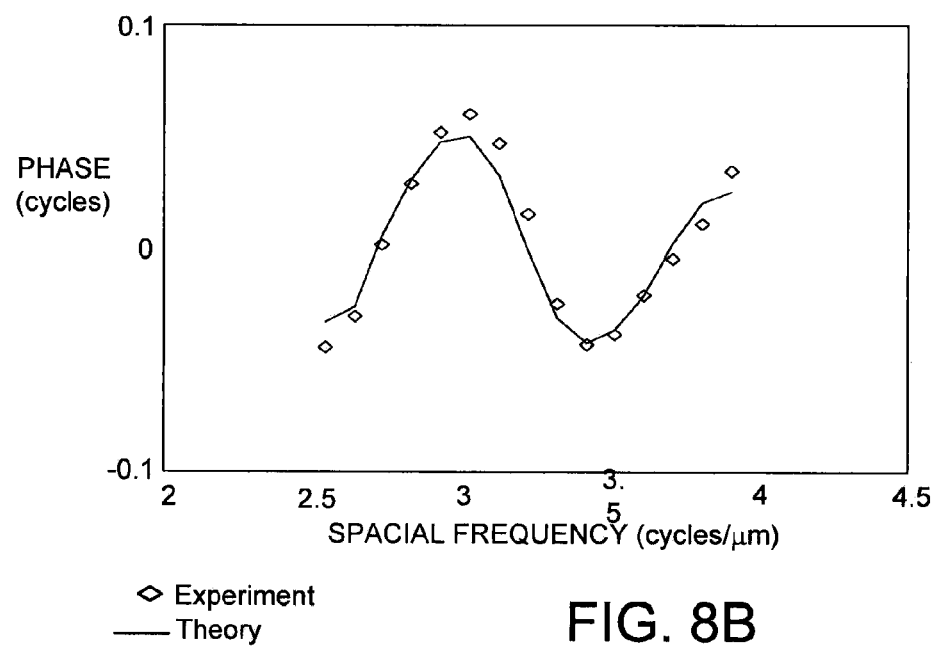

For a thin film example, we elected the same 100×, 0.78 NA Mirau objective as for FIG. 7(a), but exchanged the light source for a narrow 27-nm bandwidth LED centered at 498 nm. The sample is thin film standard of 1025 nm of $SiO_2$ on Si. Once again we observe in FIG. 7(b) a satisfying agreement between experiment and theory. The results are so close, that the difference is difficult to quantify by inspection of the signal itself. A comparison in the frequency domain, shown in FIGS. 8(a) and 8(b), indicate characteristic features of thin films, including nonlinearities in Fourier magnitude and phase that can be associated with material index and film thickness.

Referring again to FIG. 2, the model is used to provide the correspondence between the scanning distance between the regions of the fringe contrast in the interferometry signal and the actual distance between the interfaces in the sample that give rise to the different regions of fringe contrast. As shown above, the model takes into account the geometrical and spectral properties of the interferometer. For example, the model can be used to determine the separation between regions of fringe contrast for each of a series of different thicknesses for a thin film sample, for each of different illumination settings for a particular interferometer. The results of the model can then be used to provide a correspondence between the actual thickness of a thin film sample based on the separation of the between the regions of fringe contrast from an experimental interferometry signal as a function of the illuminations settings (e.g., NA and illumination bandwidth) used to collect the signal. The computer used to analyze the experimental signal may also be used to perform the numerical calculations for the model. Alternatively, the results from the modelling can be done in advance, with the resulting correspondence being stored in the computer used to analyze the experimental data in the form of scaling factors, look-up tables, and/or functions.

In some embodiments, the correspondence between the distance between the regions of the fringe contrast in the interferometry signal and the actual distance between the interfaces in the sample can be a simple scaling factor that is parametrized by the NA and the frequency bandwidth of the interferometer. For example, as described above, for a high-NA objective with a very narrow illumination frequency spectrum, one would correct for refraction distortions by multiplying by the index of refraction. We can understand this by likening the geometric limits on coherence to a focus effect. Using the paraxial lens formula, one finds that the position of best focus is shifted when entering from a vacuum into a material of index n'. The best focus position is coincident with the position of equal optical path length for the multiply-angled rays reflecting from the surface, and is consequently the position of highest fringe contrast. On the other hand, as described above, in the limit of high-bandwidth and low-NA, the scaling factor is the inverse of the group velocity index. In other words, the distance between the regions of fringe contrast in the interferometry signal is divided by the group velocity index to determine the actual distance between the sample interfaces.

Figure 9:
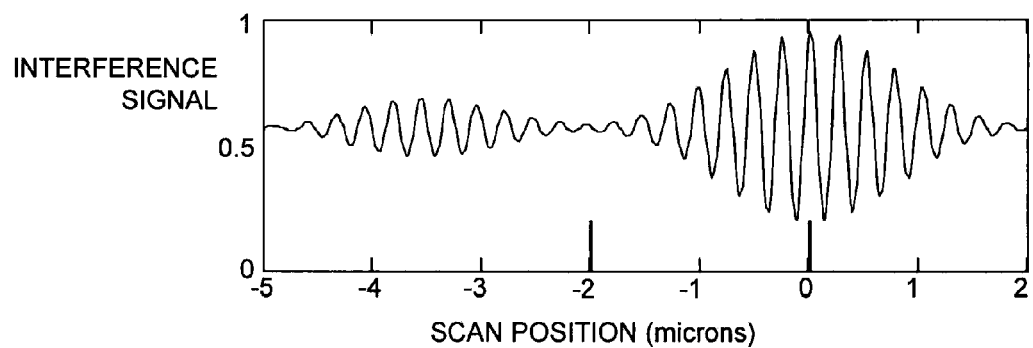
FIG. 9 is a graph of simulated interferometry signal for a 2-μm thick film of index n'=2 deposited on a substrate of index 4, viewed with a 500-nm center wavelength, 0.35 NA and 60-nm bandwidth. The left-hand peak is at about −3.75 microns, or 7n'L/8, where L is the thickness of the film.

As described above, the scaling factors are stored in a look-up table (e.g., a storage database in an electronic processor). For example, the expected results for a 60-nm bandwidth, 500-nm center wavelength with a 0.35-NA objective generates an apparent thickness of approximately 7n'L/8, as shown in FIG. 9. A close match of specific experimental conditions to these parameters implies that the true physical thickness L is 8/7n' times the apparent thickness.

In further embodiments, the correspondence may differ from such linear scaling, and may involve a non-linear relationship between the scanning distance between the regions of the fringe contrast in the interferometry signal and the actual distance between the sample interfaces for each of different illumination conditions.

In some cases, the specific interferometer used to collect the data in step 290 may have a fixed illumination frequency spectrum, but may implement various objectives with different numerical apertures depending on the specific application. In such cases, the correction factors provided in step 298, while based on the illumination frequency spectrum, may only be parametrized according the different numerical apertures of the objectives because only one illumination frequency spectrum is used. So, in some embodiments, for example, the input parameter for the illumination frequency spectrum is fixed, and need not be specified. Conversely, in other cases, the specific interferometer used to collect the data in step 290 may have a fixed NA and a variable illumination frequency spectrum (e.g., interchangeable LED sources), in which case, the correspondence between the distance between the regions of the fringe contrast in the interferometry signal and the actual distance between the sample interfaces, while based on the illumination geometry, may only be parametrized according the illumination frequency spectrum.

Figure 10:
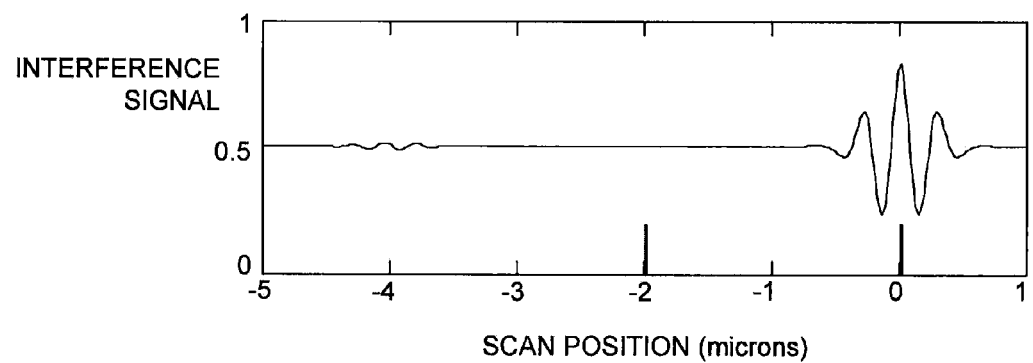
FIG. 10 is a graph of a simulated interferometry signal for an L=2-μm thick film of index n'=2 deposited on a substrate of index 4, viewed with a 500-nm center wavelength, 0.8 NA and 200-nm bandwidth. The combination of broad spectral bandwidth and high NA suppresses the underlying reflection from the substrate so that the top surface can be more easily analyzed.

In another aspect of the invention, the illumination settings can be selected to suppress the regions of fringe contrast for underlying layer(s) to allow more accurate analysis of the fringe contrast region for the top surface using, for example, conventional analysis techniques. As a result, an accurate surface profile of the top surface can be determined, even for complex samples having one or more underlying layers. Typically, this is possible, at least for visible wavelengths, with NAs greater than 0.5, and preferable greater than 0.7. This is illustrated in the simulation shown in FIG. 10 for an L=2-μm thick film of index n'=2 deposited on a substrate of index 4, viewed with a 500-nm center wavelength, 0.8 NA and 200-nm bandwidth. The combination of broad spectral bandwidth and high NA suppresses the underlying reflection. As a result, one can profile the top surface only, free of unwanted interference effects. More generally, the illumination settings necessary to suppress the contrast fringes from underlying layer can be determined using the theoretical model described above. The surface profile can be determined based on the relative change in the position of the fringe contrast region in the interferometry signal for different sample locations, using the conventional techniques described in the background. The technique described in commonly owned U.S. patent application Ser. No. 10/941,651 entitled "SURFACE PROFILING USING AN INTERFERENCE PATTERN MATCHING TEMPLATE" by Peter J. de Groot and filed Sep. 15, 2004, which was incorporated by reference and described above, can also be used.

Typically, large interference objectives having such large NAs have a correspondingly large magnification (e.g., larger than about 40×), which in turn reduces the field of view. In many applications, however, the suppression phenomenon is desired, by not at the expense of a large field of view. For example, in some applications, a sample may have multiple thin film regions separated laterally by regions having no underlying layers. In such cases it can be desirable to image an area large enough to cover multiple thin film regions or other landmarks. To achieve this result, interference objectives should be selected that have large NA (e.g., greater than 0.5, and preferably greater than 0.7), but not so large magnification (e.g., less than 10×). While such objectives are not common for interferometers, they are common in other fields such as telescope eye-pieces, and could be easily adapted for use in an interference microscope.

In preferred embodiments, the model can further include system errors for the interference microscope. As an example, a nonlinear chromatic dispersion resulting from an imbalance in refractive materials between the measurement and reference paths can be modeled as $$\upsilon(k)=\upsilon_0+(k-k_0)^2 \wp \tag{36}$$

where $\wp$ is the second-order phase dependence of $\upsilon$. This aberration leads to a broadening of the fringe contrast envelope. A similar envelope broadening for interference patterns that are limited by spatial coherence can be attributed to a nonlinear dependence of the system phase $\upsilon$ on the directional cosine $\beta$, which can result from optical aberrations.

Another example of a system imperfection is the signal integration time of the camera, which has the effect of averaging the signal over a range of scan positions. This often-called "integrating bucket" may be modeled as the convolution of a rectangular "boxcar" window with the signal. In the frequency domain, the convolution becomes the product of the Fourier coefficients q with a sync function:

$$B(K) = \frac{\sin(K\zeta_{step}/2)}{K\zeta_{step}/2}, \tag{37}$$

where $\zeta_{step}$ is the scan increment between data frames, as previously defined for Eq. (21). The effect of this time integration is to dampen the contribution from the higher spatial frequencies, as well as to reduce overall fringe contrast.

Furthermore, many system imperfections are field dependent. A relevant example is linear dispersion in the system phase υ, which changes the phase of the underlying carrier in the interference signal with respect to the fringe contrast envelope. The field dependence of the system phase behavior complicates the determination of fringe order. Modeling this phenomenon over the full image field is an example of where computational efficiency of Eq. (19) and (20) is a substantial benefit.

The data processing procedures described above can be applied to a large range of low coherence interferometry systems. For example, the light source in the interferometer may be any of: an incandescent source, such as a halogen bulb or metal halide lamp, with or without spectral bandpass filters; a broadband laser diode; a light-emitting diode; a combination of several light sources of the same or different types; an arc lamp; any source in the visible spectral region; any source in the IR spectral region, particularly for viewing rough surfaces & applying phase profiling; any source in the UV spectral region, particularly for enhanced lateral resolution; and any source or combination of sources having a net spectral bandwidth broader than 0.1% of the mean wavelength. Furthermore, the scanning system may be: driven by any of a piezo-electric device, a stepper motor, and a voice coil; implemented opto-mechanically or opto-electronically rather than by pure translation (e.g., by using any of liquid crystals, electro-optic effects, strained fibers, and rotating waveplates); any of a driver with a flexure mount and any driver with a mechanical stage, e.g. roller bearings or air bearings. Also, the interferometer optics may form any of: an interferometric microscope employing, e.g., a Mirau or Michelson objective lens; a Linnik, a Twyman Green system; a Fizeau interferometer employing a filtered or structured source spectrum so as to provide coherence peaks far from zero OPD; a fiber interferometer; and a Mach Zehnder, particularly for profiling transparent media. Finally, the data analysis may involve any of: frequency domain analysis (FDA); peak-fringe analysis; dynamic filtering to extract the fringe visibility in real time; a least-squares technique to extract fringe visibility and phase at the same time; and fringe visibility analysis followed by phase analysis, potentially including a separate measurement for phase with a modified source spectrum.

The analysis steps described above can be implemented in hardware or software, or a combination of both. The methods can be implemented in computer programs using standard programming techniques following the method and figures described herein. Program code is applied to input data to perform the functions described herein and generate output information. The output information is applied to one or more output devices such as a display monitor. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits preprogrammed for that purpose.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The computer program can also reside in cache or main memory during program execution. The analysis method can also be implemented as a computer-readable storage medium, configured with a computer program, where the storage medium so configured causes a computer to operate in a specific and predefined manner to perform the functions described herein.

The methods and systems described above can be particularly useful in any application in which one is interested in the thickness and/or surface profiles of complex samples, e.g., thin film and multilayer samples. Some exemplary applications are described below.

Semiconductor Applications

It is presently of considerable interest in the semiconductor industry to make quantitative measurements of surface topography. Due to the small size of typical chip features, the instruments used to make these measurements typically must have high spatial resolution both parallel and perpendicular to the chip surface. Engineers and scientists use surface topography measuring systems for process control and to detect defects that occur in the course of manufacturing, especially as a result of processes such as etching, polishing, cleaning and patterning.

For process control and defect detection to be particularly useful, a surface topography measuring system should have lateral resolution comparable to the lateral size of typical surface features, and vertical resolution comparable to the minimum allowed surface step height. Typically, this requires a lateral resolution of less than a micron, and a vertical resolution of less than 1 nanometer. It is also preferable for such a system to make its measurements without contacting the surface of the chip, or otherwise exerting a potentially damaging force upon it, so as to avoid modifying the surface or introducing defects. Further, as it is well-known that the effects of many processes used in chip making depend strongly on local factors such as pattern density and edge proximity, it is also important for a surface topography measuring system to have high measuring throughput, and the ability to sample densely over large areas in regions which may contain one or many surface features of interest.

Chemical Mechanical Polishing Applications

It is becoming common among chip makers to use the so-called 'dual damascene copper' process to fabricate electrical interconnects between different parts of a chip. This is an example of a process which may be effectively characterized using a suitable surface topography system. The dual damascene process may be considered to have six parts: (1) an interlayer dielectric (ILD) deposition, in which a layer of dielectric material (such as a polymer, or glass) is deposited onto the surface of a wafer (containing a plurality of individual chips); (2) chemical mechanical polishing (CMP), in which the dielectric layer is polished so as to create a smooth surface, suitable for precision optical lithography, (3) a combination of lithographic patterning and reactive ion etching steps, in which a complex network is created comprising narrow trenches running parallel to the wafer surface and small vias running from the bottom of the trenches to a lower (previously defined) electrically conducting layer, (4) a combination of metal deposition steps which result in the deposition of copper trenches and vias, (5) a dielectric deposition step in which a dielectric is applied over the copper trenches and vias, and (6) a final CMP step in which the excess copper is removed, leaving a network of copper filled trenches (and possibly vias) surrounded by dielectric material.

Figure 11A:
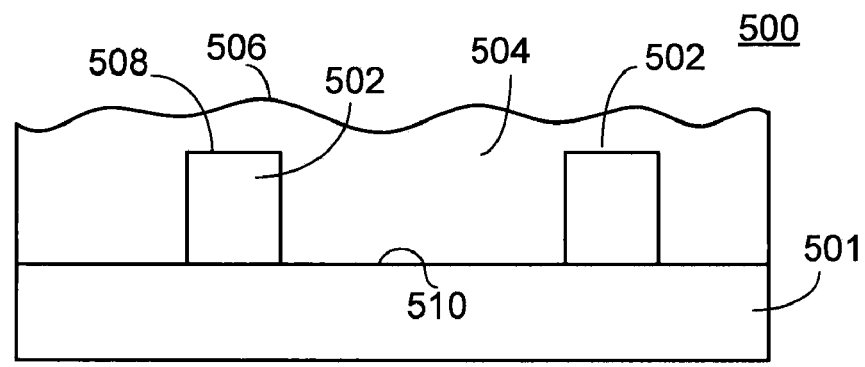
FIGS. 11a and 11b are exemplary structures having copper interconnects.

Referring to FIG. 11a, a device 500 is exemplary of the a film structure resulting from the deposition of a dielectric 504 over copper features 502 deposited on a substrate 501. The dielectric 504 has a non-uniform outer surface 506 exhibiting height variations therealong.

Figure 11B:
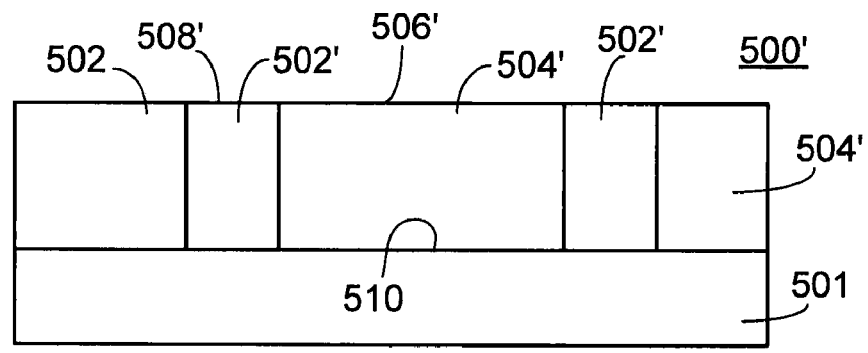

Interference signals obtained from device 500 can include interference patterns resulting from surface 506, an interface 508 between copper features 502 and dielectric 504, and an interface 510 between substrate 501 and dielectric 504. The device 500 may include a plurality of other features that also generate interference patterns. Referring to FIG. 11b, a device 500' illustrates the state of device 500 after the final CMP step. The upper surface 506 has been planarized to a surface 506', and interface 508 may now be exposed to the surroundings. Interface 510 at the substrate surface remains intact. Device performance and uniformity depends critically on monitoring the planarization of surface 504. It is important to appreciate that the polishing rate, and therefore the remaining copper (and dielectric) thickness after polishing, depends strongly and in a complex manner on the polishing conditions (such as the pad pressure and polishing slurry composition), as well as on the local detailed arrangement (i.e., orientation, proximity and shape) of copper and surrounding dielectric regions. Hence, portions of surface 506 over copper elements 502 may etch at different rates than other portions of surface 506. Additionally, once interface 508 of copper elements 502 is exposed, the dielectric and copper elements may exhibit different etch rates.

This 'position dependent polishing rate' is known to give rise to variable surface topography on many lateral length scales. For example, it may mean that chips located closer to the edge of a wafer on aggregate are polished more rapidly than those located close to the center, creating copper regions which are thinner than desired near the edges, and thicker than desired at the center. This is an example of a 'wafer scale' process nonuniformity—i.e., one occurring on length scale comparable to the wafer diameter. It is also known that regions which have a high density of copper trenches polish at a higher rate than nearby regions with low copper line densities. This leads to a phenomenon known as 'CMP induced erosion' in the high copper density regions. This is an example of a 'chip scale' process non-uniformity—i.e., one occurring on a length scale comparable to (and sometimes much less than) the linear dimensions of a single chip. Another type of chip scale nonuniformity, known as 'dishing', occurs within single copper filled trench regions (which tend to polish at a higher rate than the surrounding dielectric material). For trenches greater than a few microns in width dishing may become severe with the result that affected lines later exhibit excessive electrical resistance, leading to a chip failure.

CMP induced wafer and chip scale process nonuniformities are inherently difficult to predict, and they are subject to change over time as conditions within the CMP processing system evolve. To effectively monitor, and suitably adjust the process conditions for the purpose of ensuring that any non-uniformities remain within acceptable limits, it is important for process engineers to make frequent non-contact surface topography measurements on chips at a large number and wide variety of locations. This is possible using embodiments of the interferometry methods and systems described above.

In some embodiments one or more spatial properties, e.g., the topography of surface 506 and/or the thickness of dielectric 504, are monitored by obtaining low coherence interference signals from the structure before and/or during CMP. Based on the spatial properties, the polishing conditions can be changed to achieve the desired planar surface 506'. For example, the pad pressure, pad pressure distribution, polishing agent characteristics, solvent composition and flow, and other conditions can be determined based on the spatial properties. After some period of polishing, the spatial property can again be determined and the polishing conditions changed as needed. The topography and/or thickness is also indicative of the end-point at which, e.g., surface 504' is achieved. Thus, the low coherence interference signals can be used to avoid depressions caused by over polishing different regions of the object. The low coherence interference methods and systems are advantageous in this respect because spatial properties of the device, e.g., the relative heights of the surface of the dielectric (a) over copper elements 502 and (b) over substrate surface 510 but adjacent copper elements 502 can be determined even in the presence of the multiple interfaces.

Solder Bump Processing

Figure 12A:
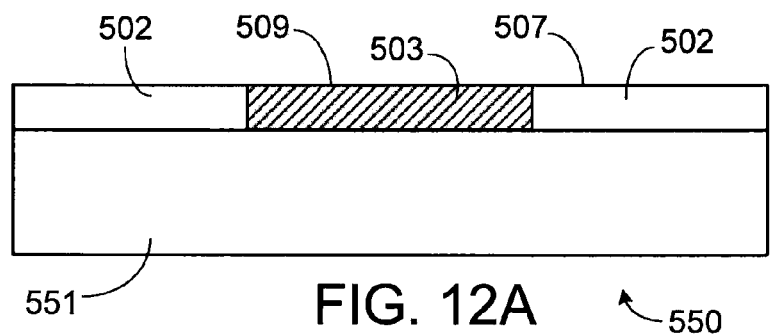
FIGS. 12a and 12b are exemplary structures formed during solder bump processing.
Figure 12B:
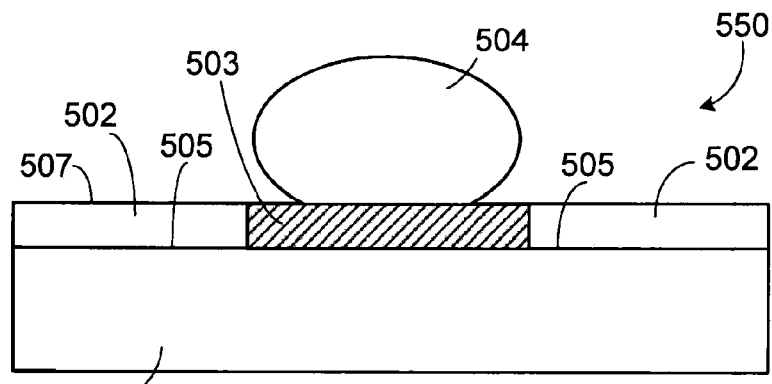

Referring to FIGS. 12a and 12b, a structure 550 is exemplary of a structure produced during solder bump processing. Structure 550 includes a substrate 551, regions 502 non-wettable by solder, and a region 503 wettable by solder. Regions 502 have an outer surface 507. Region 503 has an outer surface 509. Accordingly, an interface 505 is formed between regions 502 and substrate 501.

During processing a mass of solder 504 is positioned in contact with wettable region 503. Upon flowing the solder, the solder forms a secure contact with the wettable region 503. Adjacent non-wettable regions 502 act like a dam preventing the flowed solder from undesirable migration about the structure. It is desirable to know spatial properties of the structure including the relative heights of surfaces 507, 509 and the dimensions of solder 504 relative to surface 502. As can be determined from other discussions herein, structure 550 includes a plurality of interfaces that may each result in an interference pattern. Overlap between the interference patterns prevents accurate determinate of the spatial properties using known interference techniques. Application of the systems and methods discussed herein allow the spatial properties to be determined.

Spatial properties determined from structure 550 can be used to change manufacturing conditions, such as deposition times for layers 502,503 and the amount of solder 504 used per area of region 503. Additionally, heating conditions used to flow the solder can also be changed based on the spatial properties to achieve adequate flow and or prevent migration of the solder.

Liquid Crystal Displays

Figure 13:
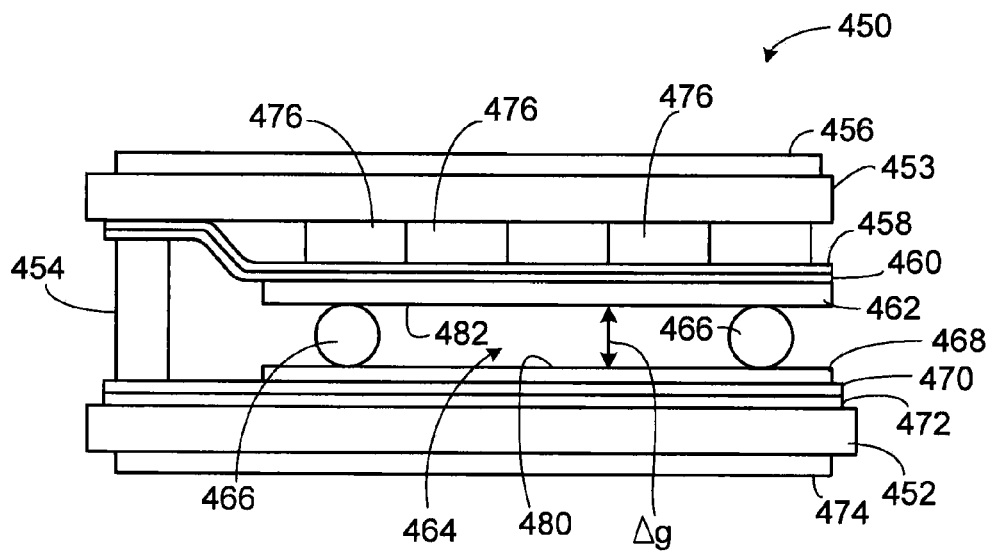
FIG. 13 is a portion of an exemplary liquid crystal display.

Referring to FIG. 13, a passive matrix LCD 450 is composed of several layers. The main parts are two glass plates 452,453 connected by seals 454. A polarizer 456 is applied to the front glass plate 453 in order to polarize incoming light in a single direction. The polarized light passes through the front glass plate 453. An Indium Tin Oxide (ITO) layer 458 is used as an electrode. A passivation layer 460, sometimes called hard coat layer, based on SiOx is coated over the ITO 458 to electrically insulate the surface. Polyimide 462 is printed over the passivation layer 460 to align the liquid crystal fluid 464. The liquid crystal fluid is sensitive to electric fields and changes orientation when an electric field is applied. The liquid crystal is also optically active and rotates the polarization direction of the incoming light. The cell gap $\Delta g$, i.e., thickness of the liquid crystal layer 464, is determined by spacers 466, which keep the two glass plates 452,453 at a fixed distance. When there is no electric potential from the front plate 453 to the rear plate 452, the polarized light is rotated 90° as it passes through the liquid crystal layer 464. When an electric potential is applied from one plate to the other plate the light is not rotated. After the light has passed through the liquid crystal layer 464, it passes through another polyimide layer 468, another hard coat layer 470, a rear ITO electrode 472, and the rear glass plate 452. Upon reaching a rear polarizer 474, the light either transmitted through or absorbed, depending on whether or not it has been rotated 90°. The cell 450 may include filters 476 or other colorizing elements to provide a color display.

The cell gap Δg determines to a great extent the optoelectrical properties of the LCD, e.g., the contrast ratio and brightness. Cell gap control during manufacturing is critical to obtaining uniform, quality displays. The actual cell gap may differ from the dimensions of spacers 466 because, during assembly, pressure or vacuum is applied to introduce the liquid crystal medium, seals 454 cure and may change dimensions, and the added liquid crystal medium generates capillary forces between plates 452,453. Both before and after adding the liquid crystal medium 464, surfaces 480,482 of plates 452,453 reflect light that results in an interference pattern indicative of the cell gap Δg. The low coherence nature of the interference signal either itself or in combination with the described interference signal processing techniques can be used to monitor properties of the cell including the cell gap Δg during manufacture even in the presence of interfaces formed by other layers of the cell.

An exemplary method can include obtaining a low coherence interference signal including interference patterns indicative of the cell gap Δg prior to adding layer 464. The cell gap (or other spatial property of the cell) is determined from the interference patterns and can be compared to a specified value. Manufacturing conditions, e.g., a pressure or vacuum applied to plates 452,453 can be changed to modify the cell gap Δg if a difference between the specified value and the determined cell gap exceeds tolerances. This process can be repeated until achieving the desired cell gap. Liquid crystal medium is then introduced into the cell. The amount of liquid crystal medium to be added can be determined from the measured spatial property of the cell. This can avoid over- or underfilling the cell. The filling process can also be monitored by observing interference signals from the surfaces 480,482. Once the cell has been filed, additional low coherence interference patterns are obtained to monitor the cell gap Δg (or other spatial property). Again, the manufacturing conditions can be changed so that the cell gap is maintained or brought within tolerances.

Laser Scribing and Cutting

Lasers can be used to scribe objects in preparation for separating different, concurrently manufactured structures, e.g., microelectronics structures. The quality of separation is related to the scribing conditions, e.g., laser focus size, laser power, translation rate of the object, and scribe depth. Because the density of features of the structure may be large, the scribe lines may be adjacent thin film or layers of the structures. Interfaces associated with the thin film or layers may create interference patterns that appear when interferometry is used to determine the scribe depth. The methods and systems described herein can be used to determine the scribe depth even in the presence of such adjacent films or layers.

An exemplary method can include scribing one or more electronic structures and separating the structures along the scribe lines. Before and/or after separation, low coherence interference signals can be used to determine the depth of scribe. Other scribing conditions are known, e.g., laser spot size, laser power, translation rate. The scribe depth can be determined from the interference signals. The quality of separation as a function of the scribing conditions, including the scribe depth, can be determined by evaluating the separated structures. Based on such determinations, the scribing conditions necessary to achieve a desired separation quality can be determined. During continued manufacturing, low coherence interference signals can be obtained from scribed regions to monitor the process. Scribing conditions can be changed to maintain or bring the scribe properties within tolerances.

A number of embodiments of the invention have been described. Nevertheless, it will be understood that various modifications may be made without departing from the spirit and scope of the invention.

What is claimed is:

1. A method comprising:
    using a microscope having a numerical aperture to illuminate a sample with test light having a frequency spectrum, where the sample includes multiple interfaces;
    combining test light reflected from the sample with reference light reflected from a reference surface to form combined light and directing the combined light to a multi-element detector;
    acquiring a signal for each element of the multi-element detector while scanning the sample relative to the multi-element detector, wherein during the scanning the reference surface remains fixed with respect to the multi-element detector and the signal for each element comprises multiple regions of amplitude variation, each region of amplitude variation corresponding to one of the interfaces; and
    determining a thickness profile or a surface height profile of the sample based on the numerical aperture, the frequency spectrum, and a separation between the corresponding regions of amplitude variation in the signal for each element.

2. The method of claim 1, wherein determining the thickness profile or the surface height profile comprises determining a distance between at least a pair of the interfaces at multiple spatial locations of the sample.

3. The method of claim 1, wherein the region of amplitude variation corresponds to the scan position where an optical path difference between test light reflected from the corresponding interface and the reference light at the multi-element detector is zero.

4. The method of claim 1, wherein the numerical aperture is greater than about 0.5.

5. The method of claim 1, wherein determining the distance between at least one pair of interfaces comprises providing information about a correspondence between the distance between the pair of interfaces and the separation between the corresponding regions of amplitude variation in the signals for different settings of the numerical aperture and the frequency spectrum.

6. The method of claim 5, wherein the correspondence is represented as a function or a look-up table that uses the information about the numerical aperture and the frequency spectrum as input parameters.

7. The method of claim 5, wherein the correspondence is based on a theoretical model for the interferometer that uses the information about the numerical aperture and the frequency spectrum as input parameters.

8. The method of claim 1, wherein the distance between the pair of interfaces is determined by determining an estimate for the distance between the pair of interfaces corresponding to the separation between the two regions of amplitude variation, and correcting the estimate based on the information about the numerical aperture and the frequency spectrum.

9. The method of claim 8, wherein the correction of the initial estimate comprises decreasing the estimate by a scale factor that increases with a group velocity index of a film corresponding to a region between the pair of interfaces.

10. The method of claim 8, wherein the correction of the initial estimate comprises increasing the estimate by a scale factor that increases with a refractive index of the film.

11. The method of claim 1, wherein the sample is a thin film sample, and the pair of interfaces is a top and bottom surface of the film.

12. The method of claim 11, wherein the sample has the film at some spatial locations and not others.

13. The method of claim 1, wherein the sample comprises a spacer element in a liquid crystal cell.

14. The method of claim 1, wherein the sample comprises a solder bump.

15. A system, comprising:

a microscope comprising an objective having a numerical aperture and comprising a reference surface and being arranged to illuminate a sample with test light having a frequency spectrum and to combine test light reflected from the sample with reference light reflected from the reference surface to form combined light;

a multi-element detector positioned to receive the combined light;

a stage configured to position the sample to receive the test light, where the system is arranged to scan the sample relative to the multi-element detector while the reference surface remains fixed with respect to the multi-element detector;

an electronic processor programmed to receive and analyze a signal from each element of the multi-element detector while the system scans the sample and to determine a thickness profile or a surface height profile of the sample, wherein each signal comprises multiple regions of amplitude variation corresponding to multiple interfaces in the sample, and the thickness profile or the surface height profile is determined based on a separation between the corresponding regions of amplitude variation in the signal for each element, the numerical aperture of the microscope, and the frequency spectrum.

16. The system of claim 15, wherein objective has a numerical aperture greater than about 0.5.

17. The system of claim 15, wherein the microscope has a magnification less than 10×.

18. The system of claim 15, wherein the microscope comprises a source having an adjustable frequency spectrum, the source being configured to provide the test light to the microscope.

19. The system of claim 18, wherein the adjustable source comprises a plurality of light sources having different emission spectrums.

20. The system of claim 15, wherein the stage is configured to position a liquid crystal display substrate to receive the test light.

21. The system of claim 15, wherein the stage is configured to position a semiconductor wafer to receive the test light.

* * * * *

UNITED STATES PATENT AND TRADEMARK OFFICE
CERTIFICATE OF CORRECTION

PATENT NO. : 7,468,799 B2  
APPLICATION NO. : 12/020351  
DATED : December 23, 2008  
INVENTOR(S) : Peter J. de Groot et al.

It is certified that error appears in the above-identified patent and that said Letters Patent is hereby corrected as shown below:

Column 24, line 7, in claim 1, delete "method" and insert --method,--.

Signed and Sealed this

Third Day of March, 2009

JOHN DOLL  
*Acting Director of the United States Patent and Trademark Office*